US011803762B2

(12) United States Patent
Rocha et al.

(10) Patent No.: US 11,803,762 B2
(45) Date of Patent: Oct. 31, 2023

(54) COMPUTER-IMPLEMENTED KNOWLEDGE MANAGEMENT PLATFORM AND A COMPUTER-IMPLEMENTED KNOWLEDGE MANAGEMENT METHOD

(71) Applicant: Semedy AG, Zug (CH)

(72) Inventors: Roberto Rocha, Wellesley, MA (US); Dirk Wenke, Kassel (DE); Thomas Krekeler, Karlsruhe (DE); Juergen Baier, Karlsruhe (DE); Saverio Maviglia, Medfield, MA (US); Daniel Rabus, Karlsruhe (DE); Dominik Aronsky, Rueschlikon (CH)

(73) Assignee: Semedy AG, Zug (CH)

( * ) Notice: Subject to any disclaimer, the term of this patent is extended or adjusted under 35 U.S.C. 154(b) by 645 days.

(21) Appl. No.: 16/902,364

(22) Filed: Jun. 16, 2020

(65) Prior Publication Data
US 2021/0390421 A1  Dec. 16, 2021

(51) Int. Cl.
*G06N 5/02*  (2023.01)
(52) U.S. Cl.
CPC ..................... *G06N 5/02* (2013.01)
(58) Field of Classification Search
CPC ........ G06N 5/02; G06Q 10/101; G16H 50/20; G16H 70/40; G06F 16/219; G06F 16/21
See application file for complete search history.

(56) References Cited

U.S. PATENT DOCUMENTS 10,678,866 B1 *  6/2020  Ranganathan ........ G06F 40/197
2008/0301142 A1 * 12/2008  Marolf .................. G06Q 10/06
707/999.009
(Continued)

FOREIGN PATENT DOCUMENTS

WO       02/071677 A2    9/2002
WO       02/082327 A1   10/2002

OTHER PUBLICATIONS

European Search Report dated Mar. 2, 2022 issued in corresponding EP Patent Application No. 21177897.2.
(Continued)

*Primary Examiner* — Phenuel S Salomon
(74) *Attorney, Agent, or Firm* — POSZ LAW GROUP, PLC

(57) ABSTRACT

A computer-implemented knowledge management platform system (KMPS) comprises at least one processor and a non-transitory memory unit that is configured to include instructions which, when performed by the processor, induce an organization of knowledge management platform items (KMPI) within a repository, wherein the KMPIs are allocated to knowledge management platform types (KMPT), which are components of a meta-modeled structure that is stored within the non-transitory memory unit and forms an object model, in particular an ontology, with at least one of the KMPTs being implemented as a core KMPT, wherein each core KMPT is attributed to each KMPI within the repository, and wherein each core KMPT defines an essential group of properties, wherein the essential group of properties of the at least one core KMPT defines lifecycle states, and wherein the meta-modeled structure is self-referential, such that each lifecycle state is stored as a KMPI within the repository itself.

26 Claims, 15 Drawing Sheets

(56) References Cited

U.S. PATENT DOCUMENTS

Figure 1:
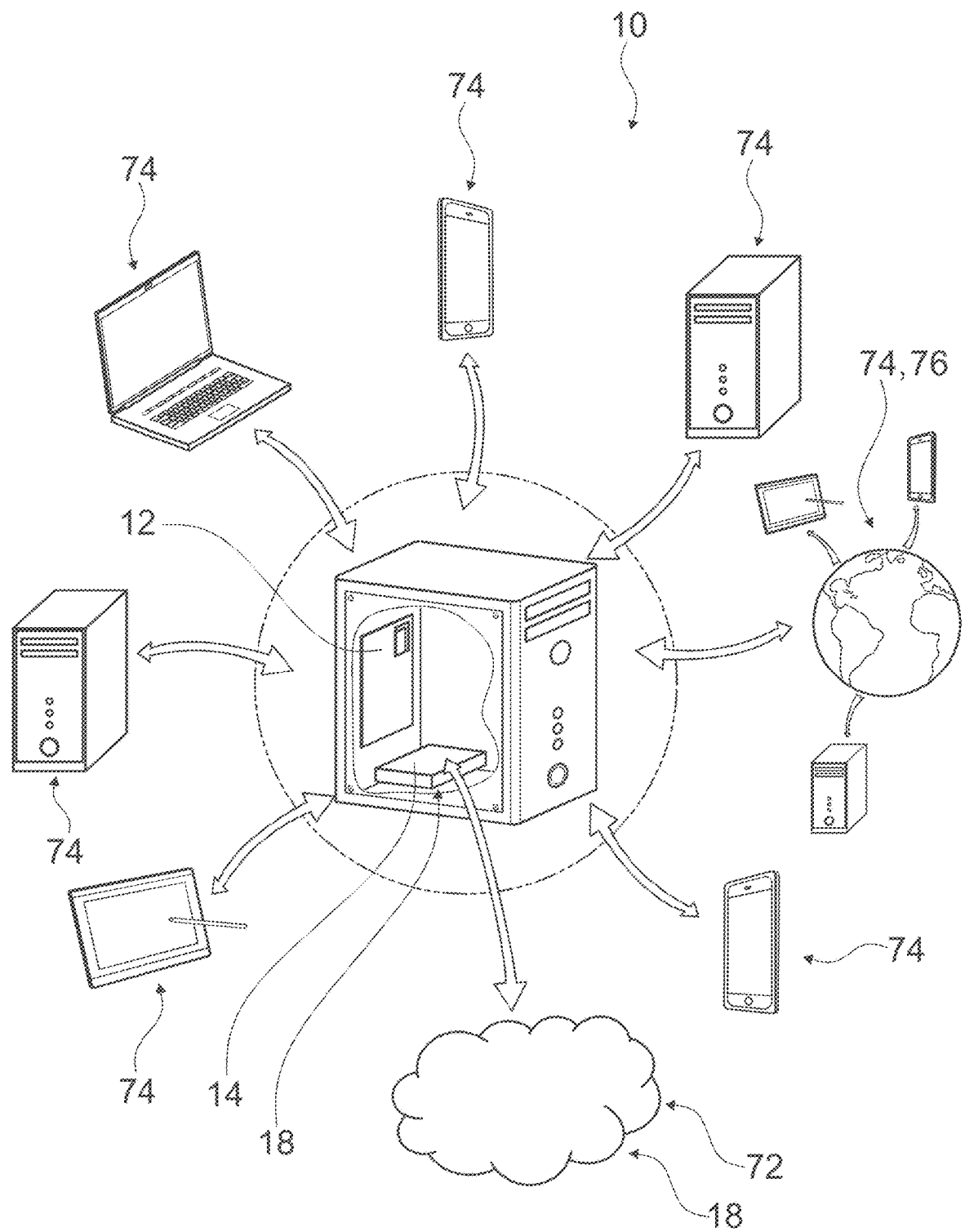

| | | | |
|---|---|---|---|
| 2010/0070448 A1* | 3/2010 | Omoigui | H01L 27/1463 |
| | | | 706/55 |
| 2013/0246049 A1* | 9/2013 | Mirhaji | G06F 40/253 |
| | | | 704/9 |
| 2014/0129504 A1* | 5/2014 | Soon-Shiong | G06N 5/022 |
| | | | 706/47 |
| 2018/0082043 A1* | 3/2018 | Witchey | G06Q 10/0633 |
| 2020/0014527 A1* | 1/2020 | Subramaniam | H04L 9/0825 |

OTHER PUBLICATIONS

Ochs, Christopher, Case, James T., and Perl, Yehoshua. Analyzing structural changes in SNOMED CT's Bacterial Infectious diseases using a visual semantic delta. _Journal of Biomedical Informatics_ 67 (2017) pp. 101-116.

* cited by examiner

# COMPUTER-IMPLEMENTED KNOWLEDGE MANAGEMENT PLATFORM AND A COMPUTER-IMPLEMENTED KNOWLEDGE MANAGEMENT METHOD

STATE OF THE ART

The invention relates to a computer-implemented knowledge management platform system (KMPS) and to a computer-implemented knowledge management method.

From the state of the art, a wide range of knowledge databases assisting experts of various professions in their daily work are known. Organizing, customizing, keeping up to date and in particular maintaining such specialized and everchanging knowledge databases is an ambitious and demanding but crucial task.

The objective of the invention is in particular to provide a system with advantageous characteristics regarding an organization and/or a consistency of knowledge assets, like knowledge management platform items (KMPI), within a knowledge database environment, in particular regarding an addition and/or a versioning of the knowledge assets (KMPI). The objective is achieved, according to the invention, by the features of the independent patent claims while advantageous implementations and further developments of the invention may be gathered from the subordinate claims.

ADVANTAGES OF THE INVENTION

In one aspect of the invention, which may be considered on its own or in combination with at least one further aspect, in particular in combination with one aspect, in particular in combination with any number of the remaining aspects of the invention, a computer-implemented KMPS, comprising at least one processor and a non-transitory memory unit that is at least configured to include instructions which, when performed by the processor, induce an organization, in particular a structuring, of knowledge management platform items (KMPI) within a repository, preferably a single repository, for example a single data repository, and is preferably configured to store the KMPIs, wherein the KMPIs are allocated and/or attributed to knowledge management platform types (KMPT), which are components of a meta-modeled structure that is stored within the non-transitory memory unit and forms an object model, in particular an ontology, with at least one of the KMPTs being implemented as a core KMPT, wherein each core KMPT is attributed to each KMPI within the repository, and wherein each core KMPT defines an essential group of properties, wherein the essential group of properties of the at least one core KMPT defines lifecycle states, and wherein the meta-modeled structure is, preferably completely, self-referential, such that each lifecycle state in turn is stored as a KMPI within the repository itself. Preferably, the self-referential meta-modeled structure causes each lifecycle state in turn to be stored as a KMPI within the repository itself. In this way advantageous characteristics regarding an organization and/or a consistency of KMPI can be achieved, leading to an advantageous high efficiency of representation and advantageous extensibility. Furthermore, by the proposed KMPS advantageous characteristics regarding maintainability can be achieved. Moreover, by the proposed KMPS an inheritability of properties can be achieved. The proposed KMPS advantageously enables an effective and customizable management of any type of knowledge, in particular of new types of knowledge. In particular by the proposed lifecycle state management an efficient and clearly organized support of controlled evolution of content and/or versioning of content can be achieved.

Moreover, by the suggested lifecycle state management, a high degree of content up-to-date-ness, and hence a high degree of content integrity, in particular a high degree of structural integrity, referential integrity and/or semantic integrity, can advantageously be achieved. Furthermore, an easy and flexible extensibility of the KMPS itself can advantageously be achieved. Moreover, by the proposed KMPS comprising lifecycle state-core KMPTs, a mechanism can advantageously be achieved which is capable of identifying a revision of a KMPI which represents the current "source of truth", i.e. the most recent or the currently valid state of the model, the KMPI, etc. In addition, the proposed KMPS comprising lifecycle state-core KMPTs advantageously provides reliable information about a history of a specific KMPI and about an evolution of a specific KMPI over time. The proposed invention advantageously provides a highly effective knowledge management system and method, which advantageously reduces a workload of a user accessing the KMPS, the workload of an administrator overseeing the KMPS, the workload of an author contributing to the KMPS and/or the energy consumption of a processing unit comprising the processor and/or the memory unit. In particular due to the fact that the KMPTs, in particular the core KMPTs, are themselves KMPTs of the KMPS, knowledge types may advantageously evolve, or new knowledge types may advantageously be created, in particular without the need for additional programming (i.e. only by user manipulation, scripting or creating rule-like statements).

The KMPS may in particular be a clinical or bio-medical knowledge management platform system. However, preferably the KMPS is capable of managing and/or organizing any kind of knowledge asset. The KMPS is in particular implemented as a computer system or at least as part of a computer system, which is preferably included in and/or has access to a large network of computer systems, e.g. an intranet (for example of a hospital or a group of hospitals) or the Internet. For example, the knowledge management platform system could be implemented as a bio-medical and/or life science knowledge management platform system which forms at least part of a health information technology infrastructure, for example within a hospital. Alternatively, the KMPS could be implemented at least partly as a virtual server, a distributed computer system and/or as a server which is part of a private or public cloud computing system. A "knowledge management platform item (KMPI)" is in particular to be understood as any kind of entity or object which is to be organized and/or accessed by the KMPS. In particular, the KMPI is a version of an entity or a version of an object, for example a version of a knowledge asset. In particular, a knowledge asset is a collection of (pieces of) information regarding a specific topic, preferably about a specific object, a specific concept, a specific method, a specific event, a specific condition or similar. For example, a knowledge asset could be an information about a specific bio-medical condition, about a specific active medication ingredient, about a specific medical procedure, etc. Preferably, the KMPI is implemented as a knowledge management platform instance. The repository could in particular be located and/or stored in the same non-transitory memory unit of the KMPS as the instructions that induce the organization of the KMPIs or alternatively in a different non-transitory memory unit of the KMPS or in a remote storage space like a cloud storage space. The KMPS enables in particular a platform model or schema which is different from a traditional database model and preferably represents a higher-level abstraction which may consolidate and integrate multiple databases or repositories. By the proposed KMPS it is advantageously easy to change and/or revise the schema (type definitions). Furthermore, in contrast to many traditional database models, the KMPS advantageously enables a simple way to keep track of the version history.

A KMPT is to be understood in particular as an entity type that is attributed to an KMPI. The KMPT preferably describes essential and non-essential properties and/or characteristics of KMPIs. For example, there could be a KMPT that describes users, a KMPT that describes organizations, another KMPT that describes associations or dependencies (undirected or directed) between KMPIs, etc. A "meta-modeled structure" is in particular to be understood as a structure which sets frames, rules and/or constraints that are applicable and useful for a generation of a model, in particular a (highly) customizable and extendable model. The KMPTs are components of this meta-modeled structure, which allow a setting of specific constraints for a specific model generated from the meta-modeled structure. Preferably, KMPTs can evolve and/or change over time. Preferably, the KMPTs are extendable into knowledge management platform subtypes. A "core KMPT" is in particular to be understood as a KMPT which is shared or may be shared across KMPIs of the KMPS and which defines an essential group of properties all KMPIs of the KMPS must possess. Preferably, the characteristics of all core KMPTs are mutually exclusive. A first core KMPT in particular comprises the first essential group of properties, which defines what identifies a KMPI, preferably in such a way that each revision and/or each instance of each KMPI is allocated and/or attributed with a universally unique identity. The first essential group of properties, in particular the identity property, preferably adopts a known Object Management Group (OMG) specification, for example Life Sciences Identifiers (LSIDs). An "identifier" is in particular to be understood as a characteristic or a property of a KMPI which uniquely defines the KMPI's identity, preferably in a standardized and cross-platform (platform independent) way. Additionally, the essential group of properties of the first core KMPT can comprise or define a revision number of an instance and a revision of a KMPI. A second core KMPT in particular comprises the second essential group of properties, which defines lifecycle states of KMPIs, preferably in such a way that each revision and/or each instance of each KMPI is allocated and/or attributed with a specific lifecycle state. A "lifecycle state" is in particular to be understood as a characteristic or a property of a KMPI which defines a status of the KMPI, in particular its activity status, preferably among several coexisting revisions or instances of the KMPI. A third core KMPT in particular comprises a third essential group of properties, which defines a provenance of each KMPI, preferably in such a way that a provenance and/or a version history of each revision and/or each instance of each KMPI is back-traceable. Additionally, the essential group of properties of the third core KMPT can comprise or define a creator and a curator of a KMPI or a specific instance or a revision of a KMPI. Additionally, the essential group of properties of the third core KMPT can comprise or define essential dates (e.g. a creation date, a modification date, an approval date, a publication date, etc.) of a KMPI or a specific instance or a revision of a KMPI. Additionally, the essential group of properties of the third core KMPT can comprise or define a source of a content of a KMPI or of a specific instance or revision of a KMPI (e.g. a treatment pathway, a coding system, etc.).

A fourth core KMPT in particular comprises a fourth essential group of properties, which defines the various names that can be assigned to each KMPI (e.g. in different languages, different symbols, different coding systems, different terminologies, different jargons, etc.), preferably in such a way that a correct KMPI can be located by different users using different names for the same object or entity. The fourth essential group of properties, in particular the name property, can be identical to the second essential group of properties (identity) but is preferably different from the second essential group of properties providing a non-opaque locating feature of the KMPI. A fifth core KMPT in particular comprises a fifth essential group of properties, which defines the context of use of each KMPI (e.g. contextual constraints, contextual exclusions, etc.), preferably in such a way that less-relevant KMPIs can be excluded at an early stage of a knowledge access procedure by a user. It is conceivable that a specific KMPS comprises all of the above-mentioned core KMPTs or only one or a fraction of the above-mentioned core KMPTs.

The meta-model of the KMPS preferably defines properties and/or groups of properties of a KMPI as attributes (simple data types, e.g. a simple string) or as relations (semantic links, structural links or any type of relationships or associations) to one or more other KMPIs. In particular by the meta-modeled structure being completely self-referential, all KMPTs, in particular all core KMPTs, are/can be themselves modeled and represented using the meta-model. In particular by the meta-modeled structure being completely self-referential, each KMPT, in particular each core KMPT, is to be stored as a KMPI within the repository itself.

The term "configure" is in particular to mean specifically to design, equip, modify, customize or extend a system or its characteristics, in particular without changes to the underlying software program. By an object being configured for a certain function is in particular to be understood that the object fulfills and/or implements said certain function in at least one application state and/or operating state. By a method being "configured" for a certain purpose is in particular to be understood that the method comprises at least one method step that is specifically directed to the purpose and/or that the method is directly focused on the purpose and/or that the method serves for fulfilling the purpose and is at least partly optimized therefor.

Moreover, it is proposed that the lifecycle states comprise at least one terminal lifecycle state and at least one non-terminal lifecycle state. This allows an advantageous organization of a KMPI, in particular of several revisions of a KMPI. In particular, an instance or a revision of a KMPI which is allocated and/or attributed with a terminal lifecycle state can be made inaccessible or not for an external user of the KMPS. In particular, an instance or a revision of a KMPI which is allocated and/or attributed with a terminal lifecycle state may or may not be accessible by a search and/or query module which is configured for providing a search functionality (a basic [lexical] search functionality and an advanced [semantic] search functionality) for a user who is looking for information and/or content within the KMPS nor by a browser module which is configured for providing a browsing functionality for a user who is looking for information and/or content within the KMPS. For example, a lifecycle state KMPI, in particular a "lifecycle asset", includes information that the KMPS applies and/or needs for organizing the KMPIs, in particular the knowledge assets (e.g. if an instance or a revision of a KMPI can be edited, if an instance or a revision of a KMPI with a given lifecycle state must satisfy specific integrity constraints, which lifecycle state of different KMPI revisions with different lifecycle states represents valid connections, etc.). In another example, a terminal lifecycle state could be a "not-publishable" lifecycle state, in particular if the corresponding instance of a KMPI contains unpublishable or incorrect content, an "obsolete" lifecycle state, in particular if the whole KMPI is to be removed, or similar. The non-terminal lifecycle states comprise for example a "work-in-progress" lifecycle state, an "under review" lifecycle state, an "approved" lifecycle state, a "published" lifecycle state, or similar. In particular, at least one of the non-terminal lifecycle states, preferably the "published" lifecycle state, marks the instance or revision of a KMPI with the highest precedence. It is conceivable that only the KMPI with the "published" lifecycle state is accessible for an external user (a user without editing powers) of the KMPS. Preferably, the lifecycle states organize the KMPIs in an authoring environment of the KMPS. In particular, the lifecycle states are a selected set of the KMPIs used within the KMPS. In particular, the "work-in-progress" lifecycle state indicates a KMPI which is in the process of being created. Preferably the KMPI with the "work-in-progress" lifecycle state is only accessible for users with edition and/or authoring power. In particular, the "under review" lifecycle state indicates that a creation process of a KMPI is completed and that the KMPI is ready to be reviewed by experts. Preferably the KMPI with the "under review" lifecycle state is only accessible for users with editing powers, users with authoring powers and/or experts with reviewing powers. In particular, a KMPI with the "work-in-progress" lifecycle state transitions into the "under review" lifecycle state upon completion of an editing of the KMPI. In particular, the "approved" lifecycle state indicates that a review process of a KMPI is successfully completed and that the KMPI is ready to be published. In particular, a KMPI with the "under review" lifecycle state transitions into the "approved" lifecycle state upon successful completion of the review process by the expert(s). In particular, a KMPI with the "under review" lifecycle state transitions into the "not publishable" lifecycle state upon a refusal of the KMPI by the expert(s) in the review process. In particular, a KMPI with the "approved" lifecycle state transitions into the "published" lifecycle state when asset is ready to be consumed by a downstream system. The above-described transitions can be semi-automatic or fully automatic. The above-described lifecycle states are exemplary, more, less or other lifecycle states are conceivable.

Furthermore, it is proposed that the lifecycle state of a KMPI with a terminal lifecycle state is immutable, and/or that the lifecycle state of a KMPI with a non-terminal lifecycle state is mutable, in particular into a "higher order" lifecycle state (higher precedence) or into a terminal lifecycle state. By this an advantageous and/or efficient organization and/or organizability of KPMIs within the repository can be achieved. In particular, it can be avoided that outdated or unpublishable instances of KMPI are accidentally revived or accidentally displayed to a user. A "higher order" lifecycle state is in particular to be understood as a lifecycle state of an instance of a KMPI which has higher precedence than the lifecycle state of another related instance of the KMPI. A generic knowledge management platform pointer (generic KMPP, see also below) always points to the revision of the KMPE (set of KMPIs) with the highest lifecycle precedence (the "highest order" lifecycle state). The above-mentioned lifecycle states for example are ordered in ascending order with the "highest order" lifecycle state at the end of the list as follows: "retired"/"not publishable" lifecycle state<"work-in-progress" lifecycle state<"under review" lifecycle state<"approved" lifecycle state<"published" lifecycle state. Other terminal and/or non-terminal lifecycle states are conceivable and could be introduced into, replaced, or removed from this list in any applicable position.

In addition, it is proposed that the KMPIs which are defined as lifecycle states include at least one instruction which is to be considered when a KMPI attributed with a respective lifecycle state and stored within the repository is organized by the processor according to instructions stored within the non-transitory memory unit. By this an advantageous and/or efficient organization and/or organizability of KPMIs within the repository can be achieved. The lifecycle states are preferably used to determine or to compute a consistency of the repository, in particular of the KPMIs within the repository. For example, a KMPI cannot refer to another KMPI with a lower precedent lifecycle state ("lower order" lifecycle state).

Furthermore, it is proposed that all KMPIs within the repository, preferably only KMPIs with a non-terminal lifecycle state, may be revisable and/or at least partially editable, wherein upon a revision of a KMPI with a non-terminal lifecycle state, which in particular is not a "work-in-progress" lifecycle state, a new instance and/or a revision of the KMPI with a newly attributed lifecycle state is created and stored within the repository. In particular all KMPIs may be revisable, however only a fraction of KMPIs may be fully or partially editable. For example, some KMPIs of designated non-terminal lifecycle states, such as the "work-in-progress" lifecycle state, are totally editable. In particular some KMPIs in other designated non-terminal lifecycle states, such as the "published" lifecycle state or the "approved" lifecycle state only allow changes to metadata of the KMPI. In particular KMPIs in terminal lifecycle states are not editable at all. By this an advantageous and/or efficient organization and/or organizability of KPMIs within the repository can be achieved. In particular, the new instance and/or the revision of the KMPI, which is generated upon a revision of a KMPI with a non-terminal lifecycle state, is allocated and/or attributed with an "initial" lifecycle state, as defined in its KMPT. The "initial" lifecycle state represents the first entry of the above-mentioned ascending list of non-terminal lifecycle states. Preferably, the initial lifecycle state is the "work-in-progress" lifecycle state.

If several consecutive instances, in particular revisions, of the KMPI are grouped within the repository, thereby forming a knowledge management platform entity (KMPE), a particularly advantageous and/or efficient organization and/or organizability of KPMIs within the repository can be achieved. In particular related KMPIs, i.e., with the same identifier (excluding revision), are grouped into a KMPE. In particular each desired modification, preferably except for a modification of attributed metadata, or each revision of a KMPI, in particular of a KMPI which is not attributed with an editable lifecycle state (for example a "work-in-progress" lifecycle state), requires a new revision/instance of a KMPI, which is then grouped into the same KMPE like the origin/predecessor KMPI.

Moreover, it is proposed that the non-transitory memory unit contains instructions which, when performed by the processor during organizing of the repository, prevent a modification of the KMPIs, except for attributed metadata, unless a specific non-terminal lifecycle state, defined as a "work-in-progress" lifecycle state, is attributed to the KMPIs. By this a high level of integrity and consistency of the externally accessible KMPIs of the KMPS can be advantageously reached. In particular, the attribution/allocation of the "work-in-progress" lifecycle state to an instance/revision of a KMPI defines if the KMPI, in particular a content of the KMPI is modifiable, in particular without creating a new revision of the KMPI, meaning without restarting a revision process within a KMPE.

If, as has already been mentioned above, the new instance of the KMPI, in particular the new revision of the KMPI, created and stored within the repository upon the revision of the KMPI, in particular upon starting a new revision process within a KMPE, is attributed the non-terminal "initial" lifecycle state, a modifiable and shapeable new instance of the KMPI is advantageously automatically made available. This advantageously improves a utility.

It is further proposed that an ensemble of all lifecycle states forms a lifecycle transition graph, which in particular defines accessibility pathways for the KMPS when accessing a KMPE. In this way an advantageous and/or efficient organization and/or organizability of KPMI within the repository can be achieved. This should in particular mean that if a user accesses the KMPS, for example using the search and/or query module or the browser module of the KMPS, the lifecycle transition graph defines which revision/instance of KMPIs within a KMPE is returned by the search and/or query module and/or displayed to the user. For example, the KMPS may only output the instance/revision of KMPIs within the KMPE, which has the highest precedent lifecycle state (the "highest order" lifecycle state, for example the "published" lifecycle state).

In addition, it is proposed that the lifecycle transition graph is customizable and/or that a plurality of lifecycle transition graphs exist simultaneously or can exist simultaneously, in particular for KMPIs attributed with different KMPTs. By this an advantageously high degree of flexibility and customizability can be achieved. In particular an order and/or a number of lifecycle states within the lifecycle transition graph are/is customizable. In particular the instructions/restrictions to the KMPS of each lifecycle state within the lifecycle transition graph are customizable. It is conceivable that a separate lifecycle transition graph can be drafted for KMPIs of specific KMPTs. For example, a lifecycle transition graph could be different for KMPIs with the KMPT "user" and for KMPIs with the KMPT "document" or for KMPIs with the KMPT "lifecycle state".

Furthermore, it is proposed that at least one lifecycle state, in particular every non-terminal lifecycle state, is only attributable to one single KMPI of a KMPE, in particular to one single revision/instance of a KMPI within a KMPE, within the repository at the same time. By this an advantageous and/or efficient organization and/or organizability of KPMIs within the repository can be achieved. In particular, only the terminal lifecycle states are attributable to more than one instance/revision of a KMPI within a KMPE. However, it is also conceivable that a maximum number of KMPIs with a specific non-terminal lifecycle state within a KMPE is customizable.

Additionally, it is proposed that a lifecycle state of a first KMPI, in particular of a first instance/revision of a KPMI, having a non-terminal lifecycle state and belonging to a KMPE is automatically changed into a terminal lifecycle state according to the lifecycle transition graph (the applied/designed lifecycle state transition diagram), when a second KMPI, in particular a second instance/revision of a KMPI belonging to the same KMPE, is attributed a "new" lifecycle state that is identical to the lifecycle state of said first KMPI. By this a high level of integrity and consistency of the KMPIs within the KMPS can be advantageously achieved.

Moreover, it is proposed that the lifecycle state of a KMPI within the repository defines if a connection and/or a linking of the KMPI to another KMPI within the repository is permitted or not. By this a high level of integrity and consistency of the KMPIs within the KMPS can be advantageously achieved. In particular a connection and/or a linking of a KMPI with a "published" lifecycle state is only possible with other KMPIs possessing a "published" lifecycle state. In particular a connection and/or a linking of a KMPI that is attributed with a "published" lifecycle state with a KMPI that is attributed with a terminal lifecycle state, with a "work-in-progress" lifecycle state or with an "under review" lifecycle state is prohibited by the KMPS. A connection and/or a linking of a KMPI with a "published" lifecycle state with a KMPI with a "approved" lifecycle state might be allowed but preferably is also prohibited by the KMPS at least as long as another KMPI of the same KMPE with a "published" lifecycle state exists. In terms of KMPPs (see also the detailed explanation and definition of pointers below), this means that a generic KMPP refers to the KMPI within a KMPE which has the lifecycle state with the highest precedence and that a KMPI cannot use a generic KMPP to refer to another KMPI of the KMPE which is attributed with a lifecycle state having a lower precedence than the KMPI of the KMPE with the lifecycle state with a higher precedence. On the other hand, a connection and/or a linking of a KMPI with an "work in progress" lifecycle state, with an "under review" lifecycle state or with an "approved" lifecycle state to a KMPI with a "published" lifecycle is allowed. Preferably all (linked) KMPIs exemplarily described in this paragraph belong to different KMPEs. Moreover, it is proposed that the lifecycle state of a KMPI within the repository defines if an editing and/or a revision of the KMPI is permitted or not. In addition, it is proposed that the lifecycle state of a KMPI within the repository defines if a KMPI must satisfy specific integrity constraints.

Furthermore it is proposed that the KMPS comprises an integrity checker module, which is configured to check the integrity, in particular the structural integrity, of a newly created and/or newly revised KMPI and/or of an existing KMPI which was attributed with a new lifecycle state, wherein upon detection of a violation of the integrity, a storing of the newly created KMPI within the repository and/or a change of the lifecycle state of the existing KMPI is prevented. By this a high level of integrity and consistency of the KMPIs within the KMPS can advantageously be guaranteed. Furthermore, advantageously a high content accuracy and completeness can be achieved. In particular the structural integrity includes range, range restrictions, cardinality, etc. Preferably the structural integrity check is part of the basic structure of the KMPS ("preprogrammed" and integral and fixed part of the KMPS), while a semantic integrity check may have to be implemented by defining (KMPS-specific) validation rules (dynamically implemented extensions of the KMPS which are KMPIs and are executed by the semantic inference unit). In particular, the integrity checker module is configured to control an evolution of KMPEs, in particular individual KMPIs of KMPEs, preferably in such a way that upon every modification of a KMPI, in particular upon every change of a lifecycle state of a KMPI, preferably upon a change of a lifecycle state into a "published" lifecycle state or upon a change of a "published" lifecycle state into a terminal lifecycle state, an integrity of all relations, pointers, links, etc. which are affected by this change is checked. Modifications or changes which lead to a violation of the integrity of the KMPS are rejected by the integrity checker module, which means that such changes cannot be saved and/or written into the memory unit which contains the repository, or the attribution/allocation of the "new" lifecycle state is prevented. Preferably, the integrity checker module is configured to control a cardinality of properties of KMPIs, to control ranges and/or range restrictions and/or to control datatype restrictions. Preferably, the integrity checker module is configured to perform lifecycle integrity checks, for example if a new or changed lifecycle state of a KMPI causes connections and/or dependencies of the KMPI to other KMPIs which are prohibited or which violate an integrity of the KMPS. Preferably the integrity checker module is implemented as a semantic and/or structural integrity checker module, which is configured to control a semantic or structural integrity of newly created and/or newly revised KMPIs and/or of existing KMPIs which were attributed with a new lifecycle state, and can be triggered ad hoc. Additionally or alternatively, the integrity checker module could be configured to actively search the KMPS, in particular the KMPI within the repository, for errors and/or unwanted situations, which in particular may or may not be caused by lifecycle state transitions. In this case, the integrity checker module would comprise one or more validation rules, which could for example be modified with (customizable) advanced search queries. The set of validation rules preferably is customizable and/or extendable. A "validation rule" is in particular to be understood as a logical expression that defines a content-dependent and customized constraint. Advanced queries can be used to implement validation rules. Validation rules themselves are implemented as KMPIs. Preferably, validation rules can run on validation rules, i.e. validation rules can be applied to validation rules. Advanced search queries are primarily, but not exclusively, semantics-based queries based on the meaning of the relationships between entities. In contrast searches preferably are just simple look-ups of word matches (simple term matches), e.g. within the repository. It is conceivable that, for example, via the search and/or query module the KMPIs with terminal lifecycle states are accessible to simple searches but not to queries (advanced search queries) due to expediency/efficiency. Thus, by continuously improving and/or extending the validation rules, the KMPS advantageously becomes smarter over time. For example, an error which is discovered once could be used to define a new validation rule in order to prevent that error from happening again in the future or in other places of the KMPS.

In addition, it is proposed that an execution of at least one checking procedure of the integrity checker module for a specific KMPI depends on the lifecycle state of said KMPI. By this computing costs can advantageously be kept low. Furthermore, unwanted error warnings about unfinished "work-in-progress" KMPIs can be avoided advantageously. In particular, an activation of the integrity checker module upon a creation and/or revision of the KMPI and/or upon a change of a lifecycle state of the existing KMPI depends on the lifecycle state of said KMPI. In particular, at least some checks of the integrity checker module that are to be performed on KMPIs are skipped if the KMPI in question has a "work-in-progress" lifecycle state. In particular, at least some checks of the integrity checker module that are to be performed on KMPIs upon a transition of lifecycle states are skipped if the transition of lifecycle states comprises a transition from a "work-in-progress" lifecycle state, from an "under review" lifecycle state or from an "approved" lifecycle state into a terminal lifecycle state, in particular into a "not publishable" lifecycle state. In particular the conditions defining when a check of the integrity checker module is skipped and when it is performed are freely adaptable, i.e. are customizable as well.

Moreover, it is proposed that the non-transitory memory unit contains at least one validation rule that is executed by the processor during an integrity check by the integrity checker module, wherein validation rules are customizable, wherein at least a customization of a validation rule itself is stored as a KMPI, and wherein a specific KMPT is allocated to each of said KMPIs containing at least one validation rule. By this a high level of integrity and consistency of the KMPIs within the KMPS can advantageously be guaranteed. By continuously improving and/or extending the validation rules via customization, thereby adapting the validation rules to a specific KMPS environment, the KMPS advantageously becomes smarter over time, while the KMPS at the same time advantageously becomes more and more error-free.

Furthermore, it is proposed that the integrity checker module comprises an inference unit, in particular at least a (extensible and/or customizable) semantic inference unit, which is configured to evaluate logical expressions within a KMPI, within a set of KMPI, in particular a set of KMPEs, and/or within the whole repository, and/or which is configured to evaluate or reason over a KMPI with related KMPIs and/or with attributes of the KMPIs. By this a high level of integrity and consistency of the KMPIs within the KMPS, in particular within the repository, can advantageously be guaranteed. An inference unit advantageously provides a level of abstraction, in particular compared to a typical relational database approach, thus advantageously increasing the usability for a standard user, and advantageously increase the flexibility to evolve the schema and represent and search or query the KMPIs more efficiently through advantageous characteristics like inheritance, versioning, and subsumption. Preferably the semantic inference unit is implemented as a semantic inference engine and/or as a semantic reasoner. The semantic inference engine is in particular configured to apply logical rules to a repository (a knowledge base), in particular to the knowledge assets and/or the KMPIs, and to deduce new information in return. In particular, in the context of the inference unit and/or in the context of the integrity checker module, the term "configured to" is not to be understood in the meaning of a configuration in the context of software programming or software modification but is rather intended to mean "specifically designed to". Preferably, the inference unit and/or the integrity checker module are extensible and/or customizable without the need for programming. Preferably, the inference unit and/or the integrity checker module are designed to allow a user to expand, limit and/or customize (semantic and/or syntactic) rules and/or settings ad hoc and/or without programming. As a consequence, it is advantageously not necessary for a user to possess programming skills and/or to go into the depths of a software to customize the inference unit and/or the integrity checker module.

A knowledge asset or a KMPI may in particular be true or relevant in some contexts but not in others. For example, a medication may be appropriate to be prescribed in one site or setting but not in another site or setting, or a disease may only affect female individuals, etc. The KMPS, in particular the semantic unit of the KMPS, enables a reasoning over explicit declarations of context. The KMPS, in particular the semantic unit, enables a distinction of different kinds of context, in particular of context which defines or constrains a KMPI or a KMPE intrinsically (the fifth core KMPT) and of context which is applied externally to an entity (e.g. an exclusion which is extrinsic to the KMPI or KMPE). An example for an intrinsic constraint is including in the fifth core KMPT a declaration that a KMPI or a KMPE is only ever relevant for a certain context, such as a pediatric medication dosing algorithm should only be considered in pediatric patients with renal or liver disfunction. An example for an extrinsic exclusion is declaring that a specific hospital has a certain medication on its formulary, which another specific hospital does not have. These contexts (constraints) together with the reasoning algorithms of the semantic unit, which are configured to evaluate logical expressions, can advantageously be used to refine a query, in particular an advanced search query, for relevant information, to contribute to semantic validation, to guide authoring of KMPIs and relationships with other KMPIs.

If modifications to KMPIs, revisions of KMPIs, inactivation processes of KMPIs and/or creation processes of KMPIs are tracked and secured via a blockchain, a particularly high level of security can advantageously be achieved. In particular an unauthorized tampering with data can advantageously be prevented. In particular the KMPS consists of a read-only component (an end user portal) and an authoring component which allows to add/import new content (the authoring workbench). The authoring workbench preferably is an environment which allows users to read and more importantly to create and curate KMPIs (e.g. order sets, treatments, arbitrary concepts). Preferably, before content is written into (committed to) the repository or the database it is validated via static consistency checks and validation rules, wherein upon a confirmation of validity, a transaction is committed (the new, the edited, the retired data and/or the KMPI is written into the repository) and an information about the transaction is written into an audit log. The audit log could in particular be part of the repository or be stored in another repository or database. In particular, via the audit log all changes and/or additions of KMPIs stored in the repository are kept track of. In the audit log, preferably at least the content of a KMPI, at least the type of a change of a KMPI, at least the creation of a KMPI and/or at least the retirement of a KMPI, an identity of a person who initiated the change of the KMPI, the creation of the KMPI and/or the retirement of the KMPI and/or a date and time when the change of the KMPI, the creation of a KMPI and/or the retirement of the KMPI was committed are/is stored. A KMPS repository can advantageously be fully reconstructed from the audit log. Preferably, any desired previous state of the KMPS is completely reconstructable from the audit log, in particular including all lifecycle states and/or all lifecycle changes of all KMPIs. In particular, the audit log can be understood as a sequence of complete "snap-shots" of all previously existing states of the KMPS, which preferably can be "rewound" to any desirable point in time since the initial setup of the KMPS and/or the start of the audit log. The audit log can advantageously prevent a tampering of the KMPS. In order to be able to detect database tampering or repository tampering, blockchain technology is advantageously used in the audit log. In order to achieve this, preferably a cryptographic hash code is stored together with each audit log item. This hash code is in particular created from both the previous hash code and the content of the current audit log item, forming a transaction block node. Advantageously, in this way it is impossible to change a single audit log item independently from the following audit log items. If in this case an audit log item is changed, then the whole chain of audit log item hashes needs to be re-calculated. In particular, in order to be able to detect such a change when the whole blockchain has been re-built, the most recent cryptographic hash code must be stored (replicated) offsite. Thus, it is advantageously very easy to detect manipulations of the database or of the repository at least by checking the integrity of the trail of the audit log and by comparing the current hash code with the hash code stored offsite. With this approach the database integrity or the repository integrity can advantageously always be verified and any prior state of the knowledge repository can be recreated.

Furthermore, it is proposed that at least one knowledge management platform designation (KMPD), which is stored within the repository and has at least one designation type, in particular a name, a code and/or a symbol, is attributed and/or allocated to at least one KMPI, in particular to at least one KMPE. By this an advantageous and/or efficient organization and/or organizability of KPMIs/KMPEs within the repository can be achieved. It is advantageous for a platform like the KMPS, which is designed to create and manage knowledge and data assets (KMPI), to enable a use of different names, codes and/or symbols, in particular to be used as KMPDs, for different types of KMPIs. For example, within the context of medical terminologies and ontologies, each discrete concept representing a disease, a symptom and/or a medication typically has multiple KMPDs, i.e. in particular names or terms, including synonyms and eponyms. The KMPDs are in particular grouped or described using "designation types". A designation type preferably defines the type of designation being represented (e.g. long name, short name, coded identifier, etc.), advantageously providing an appropriate context to help classifying similar types of names and codes. The designation type in particular also represents a specific type of the designation, including for example a differentiation of human-readable labels from non-readable symbols, bitmaps, audios, barcodes, QR codes, holograms, etc. In particular a KMPI can contain non-character-based information like symbols, bitmaps, audios, barcodes, QR codes and/or holograms. The KMPS preferably is configured to capture information about the human language that is used. The KMPS preferably allows at least one direct links between KMPDs. By this, for example, a preferred name of a given disease in a given language can be easily translated into the preferred name of the same disease in another language. Similarly, by this the preferred name of a given disease can advantageously also be easily cross-referenced with an appropriate code from a specific coding system. This advantageously flexible and extensible representation of designations helps users in a searching for and/or retrieval of knowledge assets, in particular of KMPIs, using terms that the users are familiar with, while also advantageously enabling efficient translations and cross-references.

If a number of KMPDs which are attributable to the at least one KMPI, in particular the at least one KMPE, is unlimited, a high flexibility and/or completeness of the KMPS can advantageously be achieved.

If additionally each KMPT, in particular each core KMPT, is customizable, wherein at least a customization of a KMPT, in particular a core KMPT, itself is stored as a KMPI, and wherein a customized KMPT, in particular a customized core KMPT, inherits all customized and non-customized properties of the bequeathing KMPT, in particular the bequeathing core KMPT a usability can advantageously be improved. Additionally, a high level of integrity and consistency of the KMPS can advantageously be guaranteed. Preferably, a customized KMPT, in particular a customized core KMPT, inherits all customized and non-customized designation types of the bequeathing KMPT, in particular the bequeathing core KMPT.

Preferably, a KMPI can inherit from one KMPT (core KMPT) and/or from more than one KMPT (core KMPT).

Moreover, a computer-implemented knowledge management platform system (KMPS) is proposed, which comprises at least one processor and a non-transitory memory unit that is configured to store knowledge management platform items (KMPI) and to include instructions which, when performed by the processor, induce an organization of the KMPI within a repository, wherein several consecutive instances, in particular revisions, of the KMPIs are grouped within the repository, thereby forming a knowledge management platform entity (KMPE), wherein the KMPIs are allocated to knowledge management platform types (KMPT), which are components of a meta-modeled structure that is stored within the non-transitory memory unit and forms an object model, in particular an ontology, with at least one of the KMPTs being implemented as a core KMPT, wherein each core KMPT is attributed to each KMPI within the repository, and wherein each core KMPT defines an essential group of properties, wherein the group of properties of the at least one core KMPT defines lifecycle states, and wherein the non-transitory memory unit is configured to store knowledge management platform pointers (KMPP), each of which is assignable to at least one KMPI of a KMPE and which are at least configured to link the at least one KMPI with at least one target KMPE within the repository and/or with at least one other KMPI within the repository, and wherein the meta-modeled structure is, preferably completely, self-referential, such that each lifecycle state and each KMPP is in turn stored as a KMPI within the repository itself. Preferably, the self-referential meta-modeled structure causes each lifecycle state and each KMPP in turn to be stored as a KMPI within the repository itself. By this an advantageous and/or efficient organization and/or organizability of KPMIs/KMPEs within the repository can be achieved. In particular, the KMPPs are employed to establish relations, which preferably in turn define dependencies or semantic connections between KMPIs and/or between KMPEs.

In particular in a KMPS with highly interconnected KMPIs/knowledge assets, versioning of the assets introduces major challenges concerning the question when to update which connections. Especially in a KMPS with large data repositories/large numbers of KMPIs, an updating of connections advantageously needs to happen in an automated fashion, as manual maintenance of the connections is not manageable. The KMPS described herein suggests a mechanism called KMPP to update these connections in a consistent, reliable and deterministic manner. In particular, to be able to do this in an automated fashion, there exists at least one fundamental rule that the KMPS must follow: a modification of a KMPI, in particular apart from modifications of metadata, can only be implemented as a new revision of the KMPI if the modification does not change the meaning of the KMPE, the KMPI belongs to. In particular, if the meaning of the KMPE is altered, a completely new KMPI belonging to a completely new KMPE must be created. In particular, when creating connections (KMPP), the creator of the KMPPs decides whether the connections (KMPP) should update automatically (generic KMPPs) or should refer to the revision of the target as initially defined (revision-specific KMPPs). Preferably a connection target of a generic KMPP is always the revision of the target KMPI with the highest precedence lifecycle state.

It is further proposed that at least one group of KMPPs is implemented as generic KMPPs, and that the non-transitory memory unit contains instructions which, when performed by the processor, induce an automatic updating of each generic KMPP pointing to a target KMPE upon detection of at least one revision of the target KMPE, preferably upon detection of a change of a lifecycle state of the current revision with the highest precedence of the KMPIs of the KMPE (which could for example be the "published" revision or instance of KMPIs of the KMPE) and/or upon detection of a change of a lifecycle state of a newer revision or instance of KMPIs of the KMPE into the lifecycle state with the same level of precedence or into the same lifecycle state. By this an advantageous and/or efficient organization and/or organizability of KPMIs/KMPEs within the repository can be achieved. In particular, the KMPP and/or the target of the KMPP is updated at the time when a different revision or instance of KMPIs of a KMPE becomes the revision with the highest precedence of all KMPIs within the KMPE (e.g. when a KMPI of a KMPE is allocated/attributed with the "published" lifecycle state, thereby retiring the previously published KMPI of the KMPE). An example for a generic KMPP would be an order set (order set KMPI) for immunomodulator which relates to medications (medication KMPIs) that can be prescribed for autoimmune disorder, like adalimumab. If now, for example, a new revision of the adalimumab-KMPI is created including updated information about possible side effects (which is no change in the meaning of the KMPE "adalimumab"), the relation from the order set KMPI should be updated to refer to the updated adalimumab-KMPI revision. In particular, when the new revision within the adalimumab-KMPE (i.e. the new adalimumab-KMPI) is created (attributed with a "work-in-progress" lifecycle state), the published order set KMPI will still relate to the previous revision of adalimumab, which is currently published (the current adalimumab-KMPI with the "published" lifecycle state). However, in particular at a point when the newly created adalimumab-KMPI revision is published (i.e. attributed with the "published" lifecycle state) and thus retires the "old" published revision of adalimumab-KMPI, the relation of the order set KMPI will automatically be updated by KMPS when using a generic pointer to point to the newly created adalimumab-KMPI. Preferably, the connection made by the generic KMPP always, in particular automatically, points to a KMPI with a non-terminal lifecycle state of the target KMPE, in particular a KMPI with a "published" lifecycle state of the target KMPE. All KMPIs can be browsed or searched and/or queried by a user of the KMPS, in particular the search and/or query module or the browser module, or which can be displayed to a user via the end user portal of the KMPS. However, since the KMPS provides many customization possibilities, this ability to search and/or query for all KMPIs could also be removed or altered.

It is additionally proposed that at least one group of KMPPs is implemented as revision-specific KMPPs, which are configured to always point to a specific KMPI of a target KMPE, in particular even after a revision of the target KMPE. By this an advantageous and/or efficient organization and/or organizability of KPMIs/KMPEs within the repository can be achieved. An example for a revision-specific KMPP would be a KMPI which is a discussion about a content of a specific revision of a KMPI, in particular a specific KMPI of a KMPE. This discussion should in particular always refer to the exact revision of the KMPI, in particular to the exact same KMPI of a KMPE. Another example is the relationship between a KMPI and its KMPTs, which must be also a revision-specific KMPP.

Furthermore, it is proposed that the lifecycle state of the at least one KMPI within the repository defines whether an assignment of a specific KMPP to the at least one KMPI and/or a pointing of the specific KMPP to a target KMPI and/or KMPE is permitted or not. By this an advantageous and/or efficient organization and/or organizability of KPMIs/KMPEs within the repository can be achieved. Preferably, a KMPP is assigned to a certain KMPI or KMPE, which then constitutes a starting point or an origin of the KMPP. The KMPI or KMPE of the end point or target of the KMPP is thereby referenced by the KMPI or KMPE or by the starting point of the KMPP.

Moreover it is proposed that a KMPP assigned to a KMPI of a KMPE, in particular a KMPI with a non-terminal lifecycle state of a KMPE, for example to a KMPI with a "published" lifecycle state of the KMPE, is only permitted to point to other KMPEs with compatible lifecycle states, in particular to other KMPEs containing a KMPI with a non-terminal lifecycle state, and/or to other KMPIs with lifecycle states of equal or higher precedence ("order"). By this an advantageous and/or efficient organization and/or organizability of KPMIs/KMPEs within the repository can be achieved. A compatible lifecycle state of the "published" lifecycle state in this sense is, for example, only the "published" lifecycle state. Compatible lifecycle states of the "approved" lifecycle state in this sense are, for example, the "published" lifecycle state and the "approved" lifecycle state. In particular the compatible lifecycle states are defined by the lifecycle transition model of the KMPS. In particular the compatible lifecycle state definition could be part of one or more lifecycle transition schemas of the KMPS. The compatible lifecycle states are (similarly to the lifecycle transition schemas) customizable. If, for example, as suggested before for the "approved" lifecycle state, it is defined that compatible states are the "approved" lifecycle state and the "published" lifecycle state, this will mean that a KMPI revision and/or a KMPI of a KMPE with the "approved" lifecycle state can have relations to other KMPI revisions and/or to other KMPIs of a KMPE, which are either attributed with the "approved" lifecycle state or with the "published" lifecycle state. A relation to a KMPI with a different lifecycle state would be considered a violation of the lifecycle compatibility constraints and would preferably be prevented by the integrity checker module and/or by the semantic unit. In particular the integrity checker module checks upon a creation and/or upon a change of a relation, in particular of a KMPP, if the resulting relation, in particular the resulting KMPP, is permitted or not.

In addition it is proposed that the KMPS comprises at least one knowledge management platform association (KMPA), which is in particular configured to define a ad-hoc or non-definitional relation, and which is stored as a KMPI within the repository itself, wherein the KMPA at least comprises information about a source KMPI, about a target KMPI and about a concrete relation between the source KMPI and the target KMPI. By this a particularly easy and flexible content creation or authoring of (interrelated) KMPEs can advantageously be achieved. While in particular the authoring workbench operates on a declarative content model, the read-only environment (the end user portal) preferably operates on a production content model. The production content model is in particular derived from the declarative model and represents a final state of the KMPS that is consumed by end users. A declarative content model, in particular, includes all KMPIs of a KMPE that are facts or rules; whereas the production model only includes facts, whether asserted or inferred. Rules, in particular, are instructions that the semantic inference unit uses to infer new facts. Such a separation advantageously enables creators and/or authors, besides a creation of type (KMPT) definitions with respective properties and concrete instantiations, to define the ad-hoc or non-definitional relations (KMPA). The KMPAs advantageously enable the creators and/or authors to establish connections between KMPIs and/or KMPEs without the need to revise. Preferably, during a production model generation the KMPAs (the ad-hoc or non-definitional relations) are converted into KMPPs (full-fledged relations). Advantageously, the end users therefore do not have to distinguish between different kinds of relations. For example, the information about the concrete relation between the source KMPI and the target KMPI could be an information like "similar to", "equal to", "has indication", "is manifestation of", etc.

Moreover it is proposed that the KMPS comprises an authoring component, in particular an authoring workbench, and a read-only component, in particular an end user portal, wherein the KMPA is converted into a KMPP upon a transformation from the authoring component, in particular the authoring workbench, to the read-only component, in particular the end user portal. By this search and/or query performance and user experience is considerably improved. For example, the end users advantageously do not have to distinguish between different kinds of relations, whereby a particularly easy and flexible content creation or authoring of (interrelated) KMPEs can advantageously be achieved. An example for a KMPA is an information that a medication can be used as a replacement for a different medication. Preferably such an information should not be stored at the level of the related medications, as it does not define the meaning of orderables. In addition, such connections should preferably be addable and/or removable without a need to revise concrete orderables. Advantageously such relations can be defined as KMPAs containing the information about the source KMPE or KMPI ("different medication"), the target KMPE or KMPI ("medication") and the concrete relation between them ("replaced by"). In this way, advantageously, the information about this KMPA is clearly separated from the information about the orderables in the declarative model. In particular during the generation of the production model, the KMPA is converted into a KMPP and end users of the end user portal will see them as regular relations. In particular a read-only component that is separated from the authoring workbench is required in order to be able to advantageously support a transactional use of the repository (authoring versus read-only). Furthermore, the read-only component advantageously represents a snap-shot in time.

In addition, it is proposed that the KMPS comprises an integrity checker module, which is configured to automatically check the integrity of KMPPs created by inference upon a transition from the authoring component to the read-only component, preventing the transition and/or prompting a warning in case an integrity violation is detected. By this a high degree of integrity and/or consistency can advantageously be achieved. It is conceivable that the semantic inference unit is used to generate read-only versions that are differently represented than in the authoring component. For example, a change in format and/or in transformation may be applied by the semantic inference unit. Furthermore, it is conceivable that the semantic inference unit, is applied to separate "inferred facts" and "asserted facts" in order to only propagate "asserted facts" from the authoring component into the read-only component.

Furthermore, a computer-implemented knowledge management method with a knowledge management platform system (KMPS) is proposed, comprising at least one processor and a non-transitory memory unit that is configured to store knowledge management platform items (KMPI) and to include instructions which, when performed by the processor, induce the KMPS to organize the KMPIs within a repository, wherein the KMPIs are allocated to knowledge management platform types (KMPT), which are components of a meta-modeled structure that is stored within the non-transitory memory unit and forms an object model, in particular an ontology, wherein at least one of the KMPTs is implemented as a core KMPT, wherein each core KMPT is attributed to each KMPI within the repository, and wherein each core KMPT defines an essential group of properties, wherein the group of properties of the at least one core KMPT defines lifecycle states, and wherein the meta-modeled structure is, preferably completely, self-referential and, as a result of this, each lifecycle state is in turn stored as a KMPI within the repository itself. In this way advantageous characteristics regarding an organization and/or a consistency of KMPIs can be achieved, leading to an advantageous high content accuracy, integrity, completeness and maintainability. Moreover, by the suggested lifecycle state management, a high degree of content up-to-date-ness, and hence a high degree of content integrity, can advantageously be achieved.

A computer-implemented knowledge management platform system according to the invention and a computer-implemented knowledge management method according to the invention are herein not to be restricted to the applications and implementation forms described above. In particular, to fulfill a functionality herein described, the computer-implemented knowledge management platform system according to the invention and the computer-implemented knowledge management method according to the invention may comprise a number of respective elements and/or structural components and/or units and/or method steps that differs from a number herein mentioned.

DRAWINGS

Further advantages will become apparent from the following description of the drawings. In the drawings an exemplary embodiment of the invention is depicted. The drawings, the description and the claims contain a plurality of features in combination. Someone skilled in the art will purposefully also consider the features separately and will find further expedient combinations.

Figure 2:
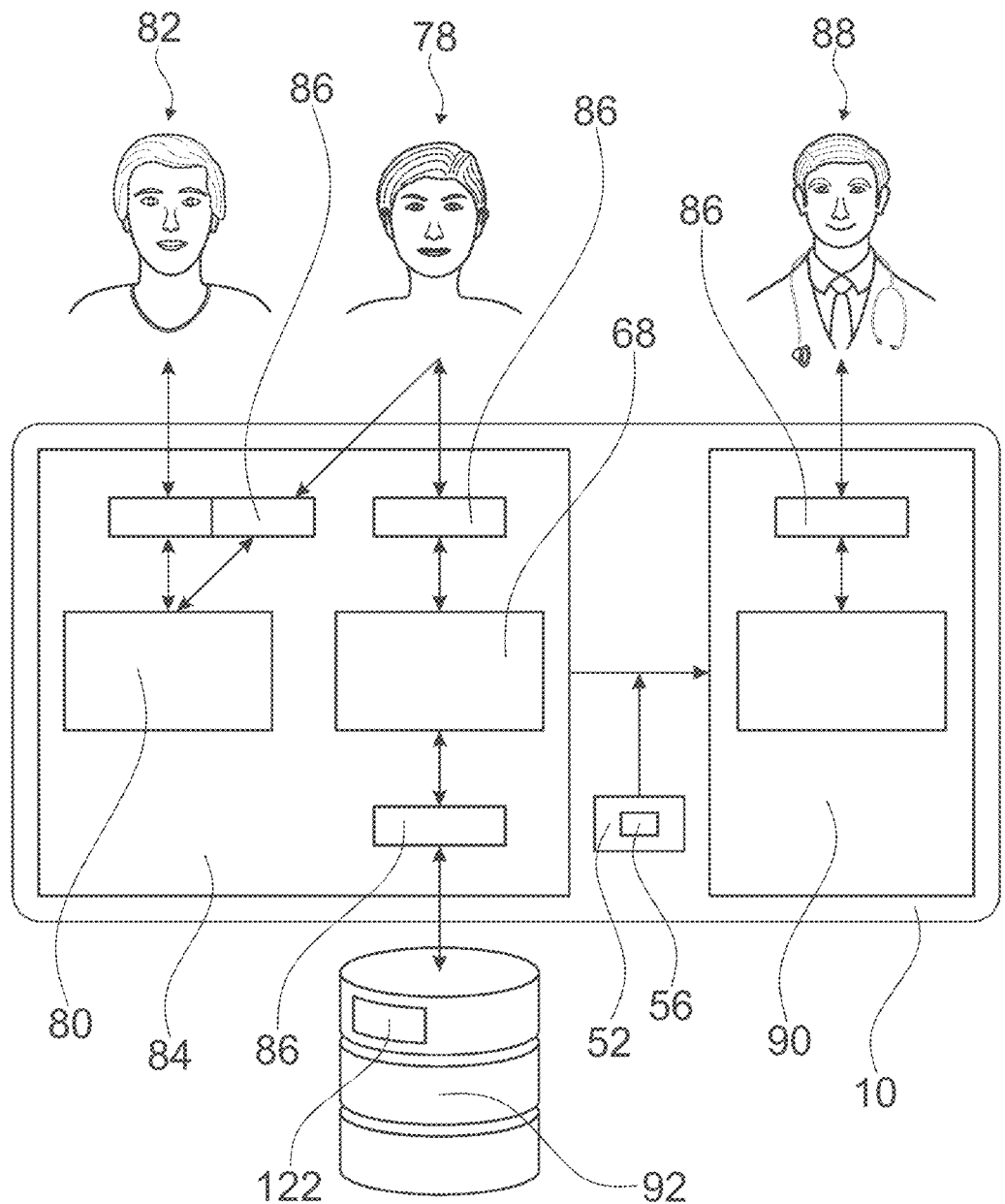
Figure 3:
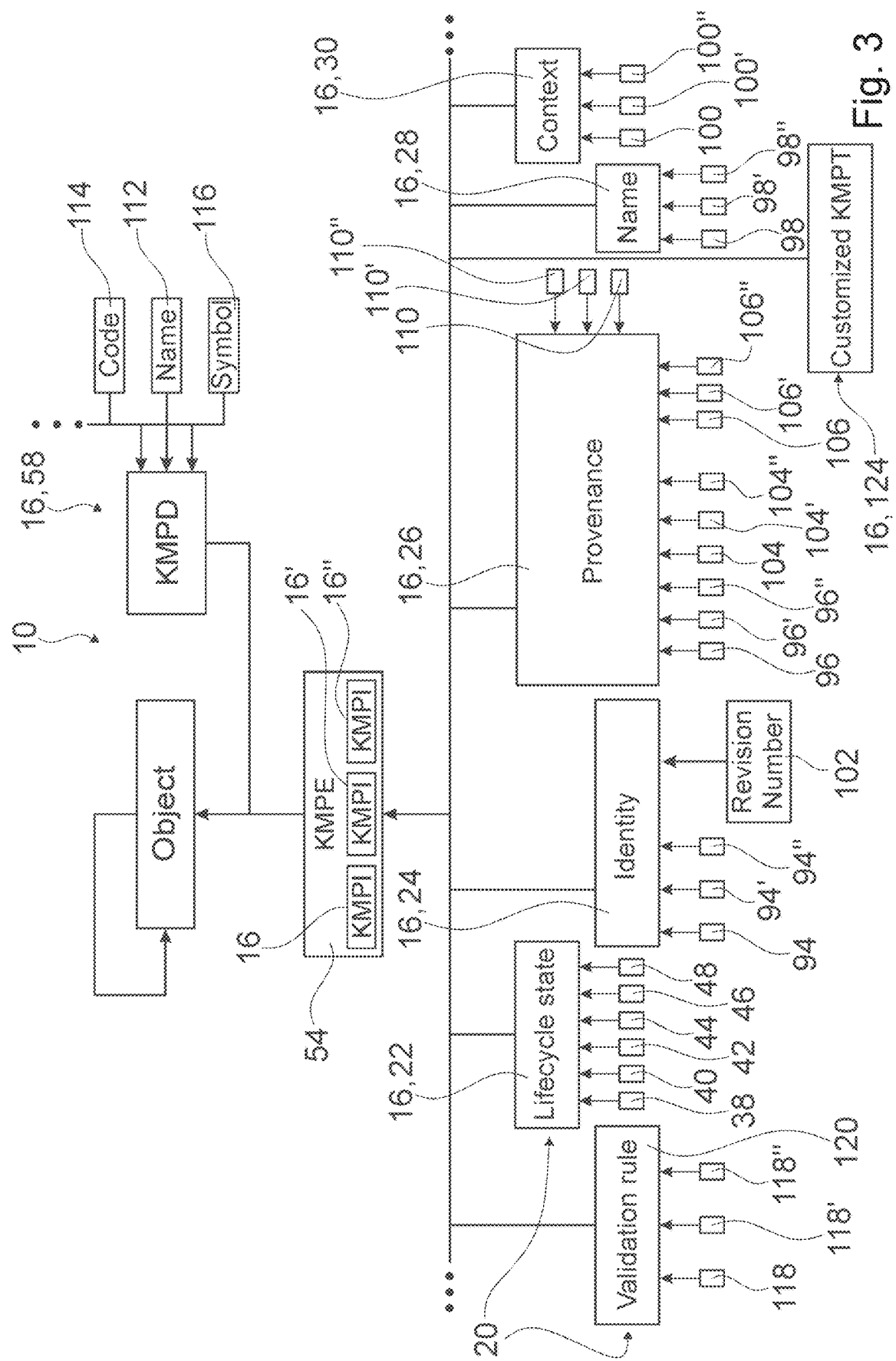
Figure 4:
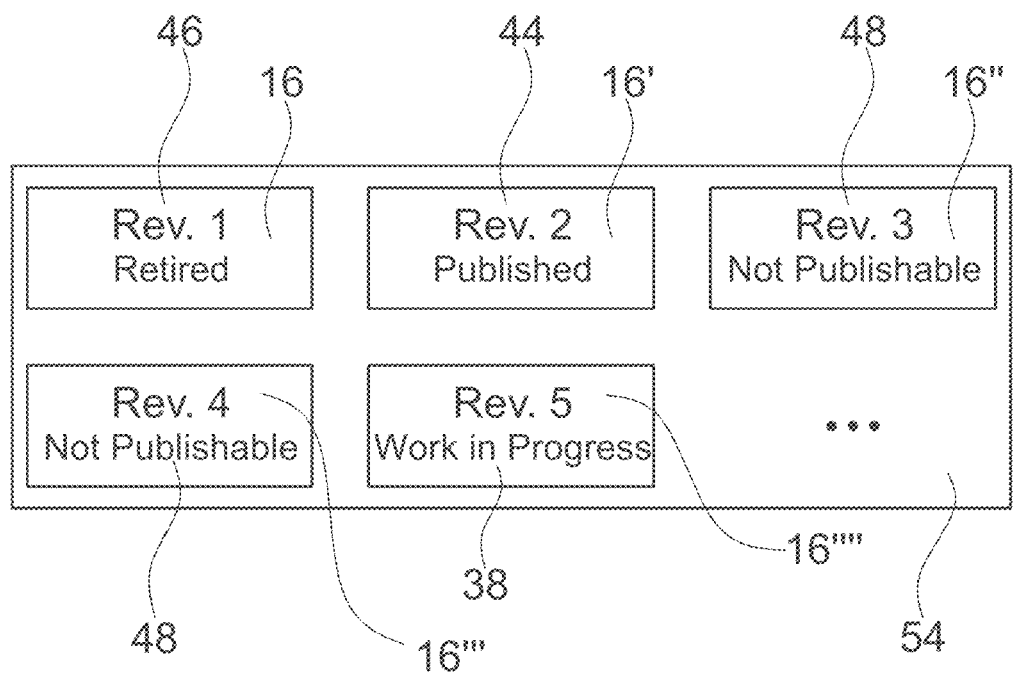
Figure 5:
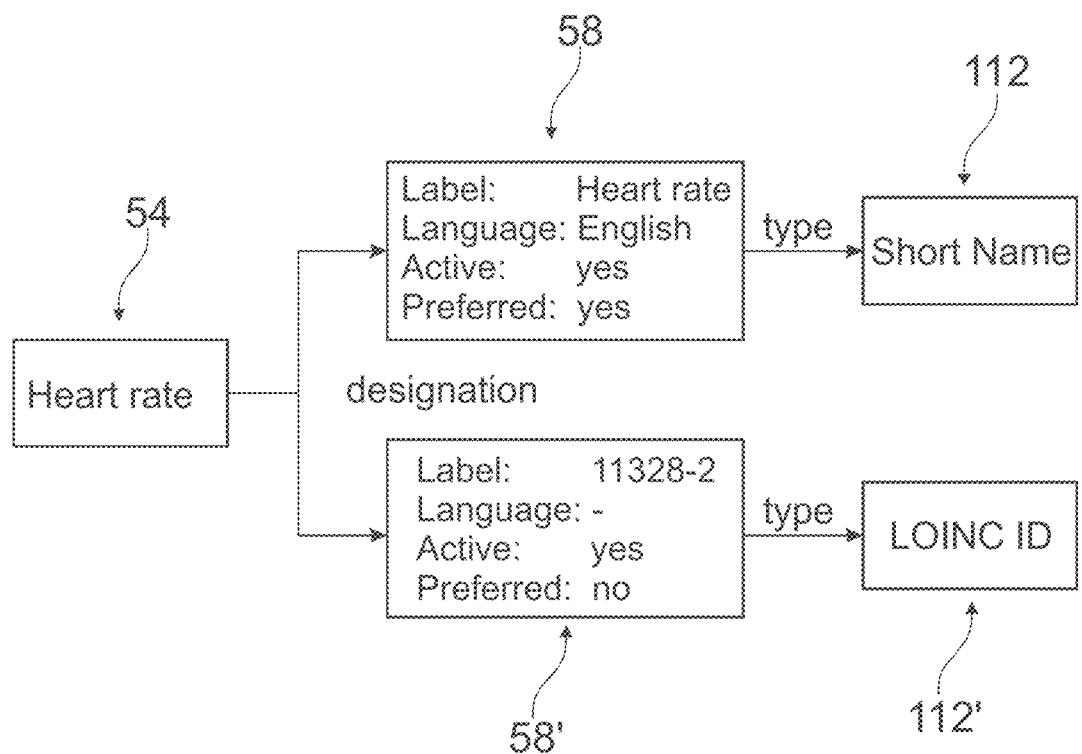
Figure 6:
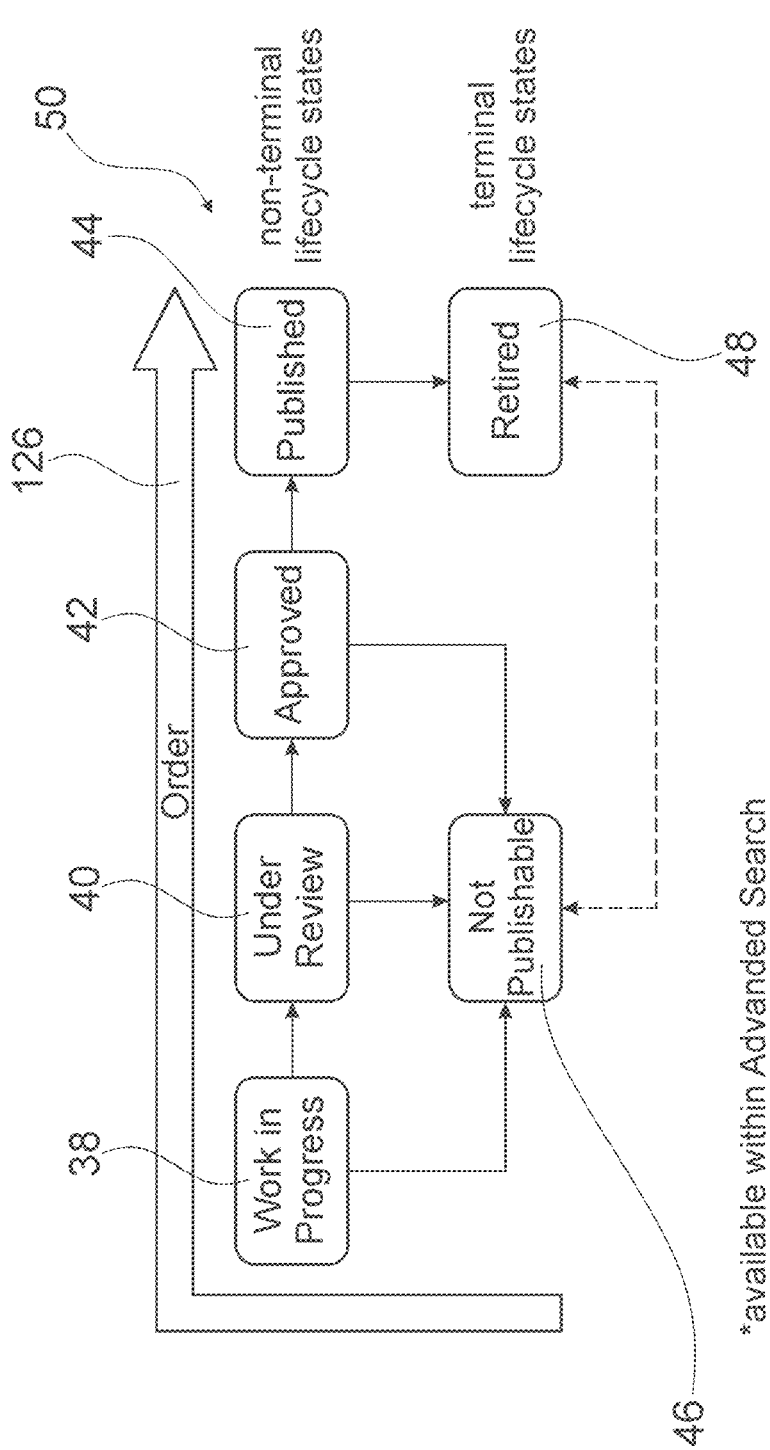
Figure 7A:
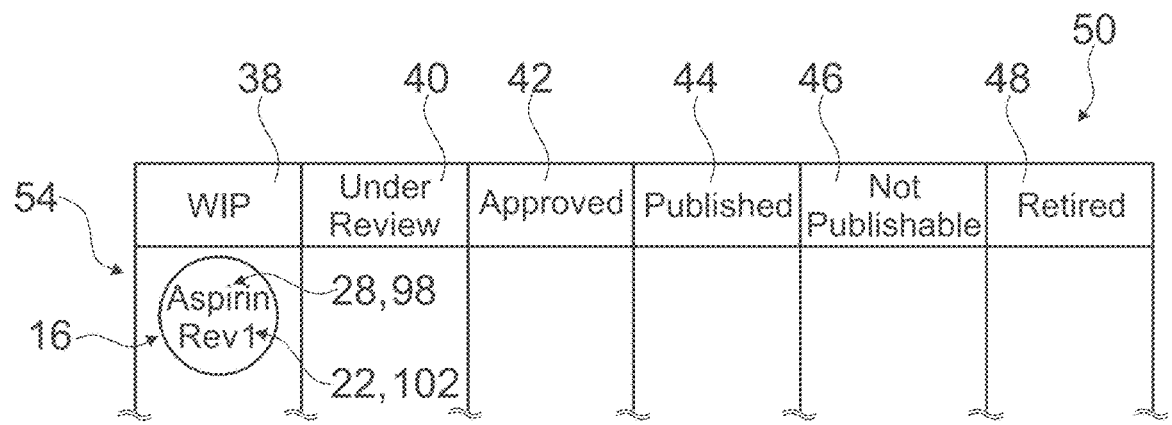
Figure 7B:
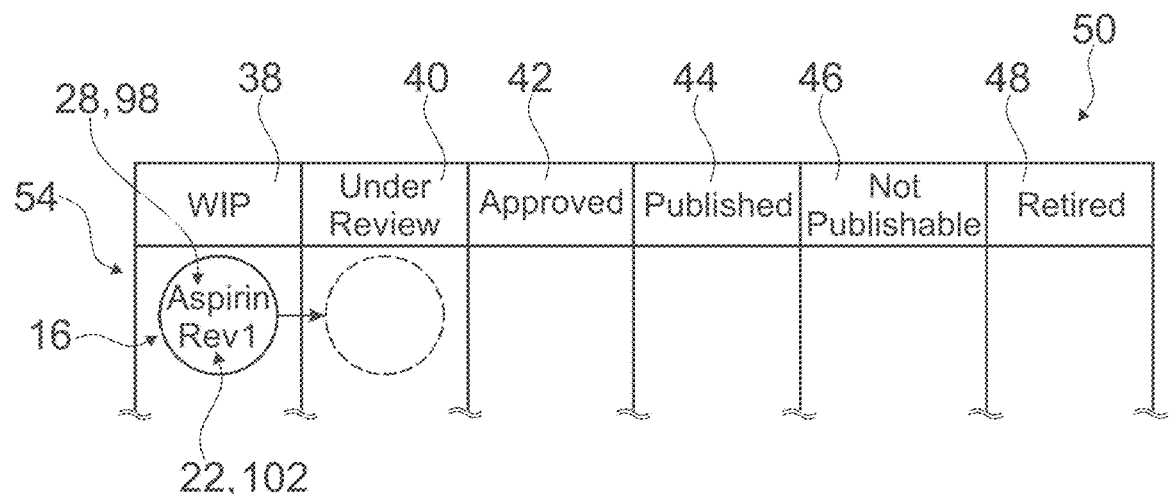
Figure 7C:
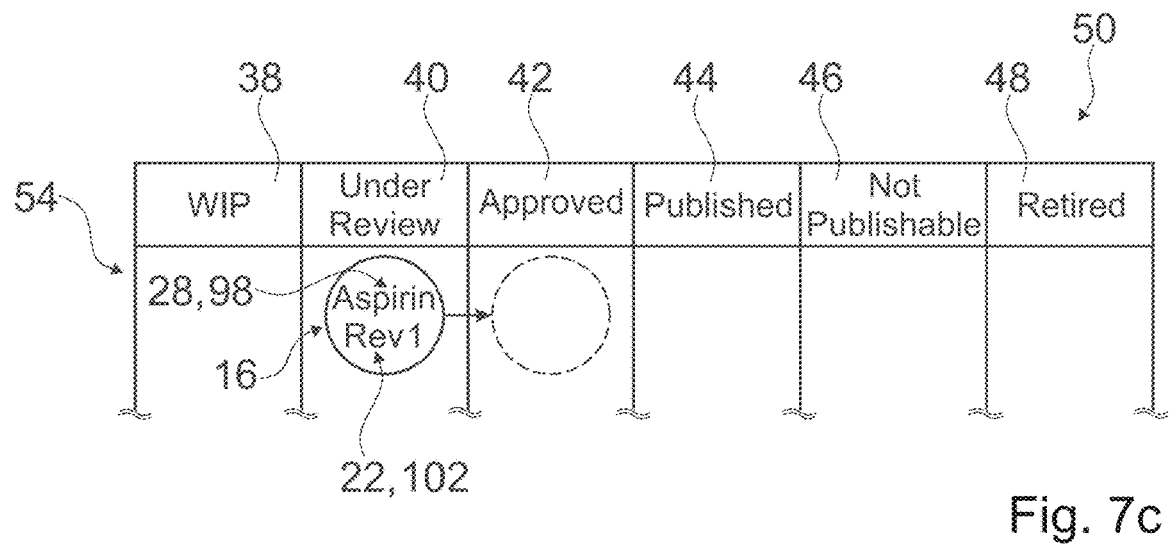
Figure 7D:
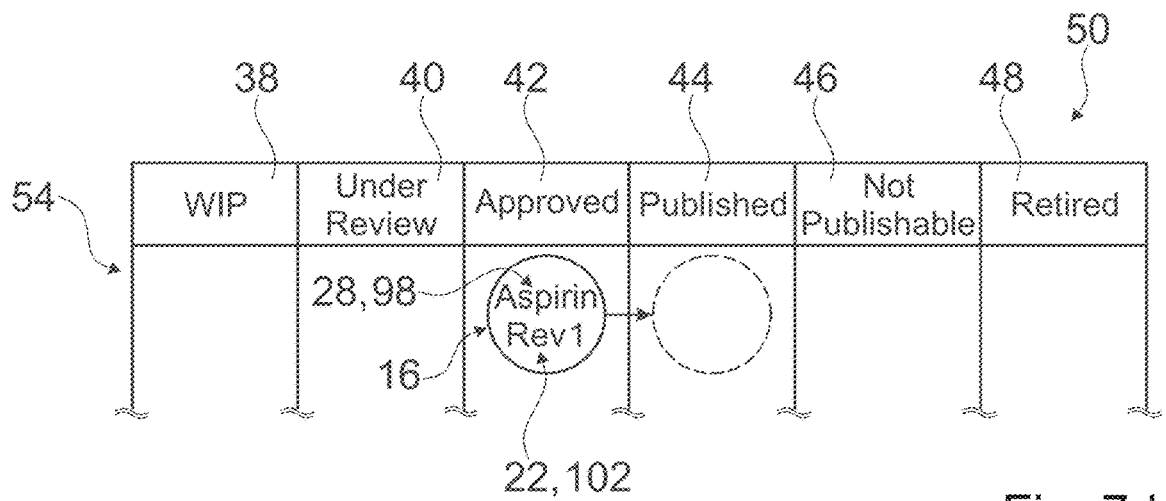
Figure 7E:
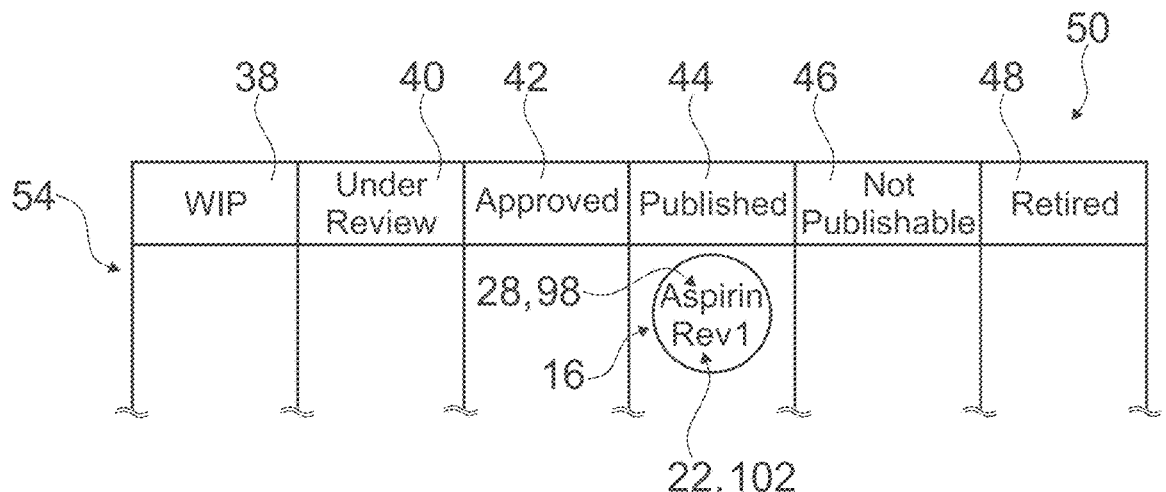
Figure 7F:
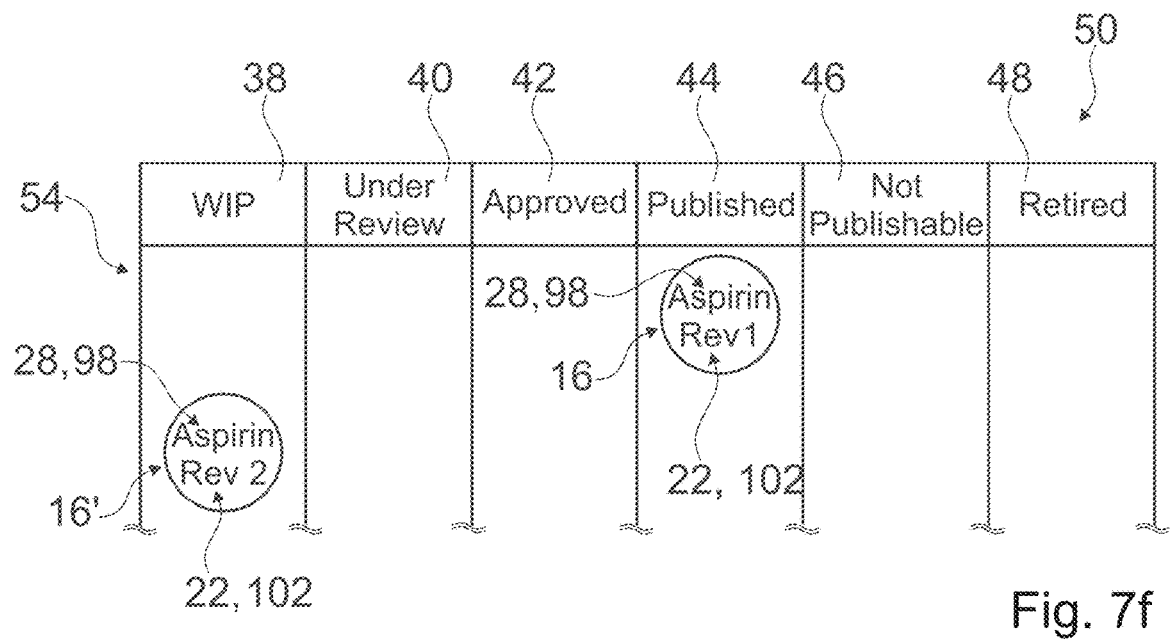
Figure 7G:
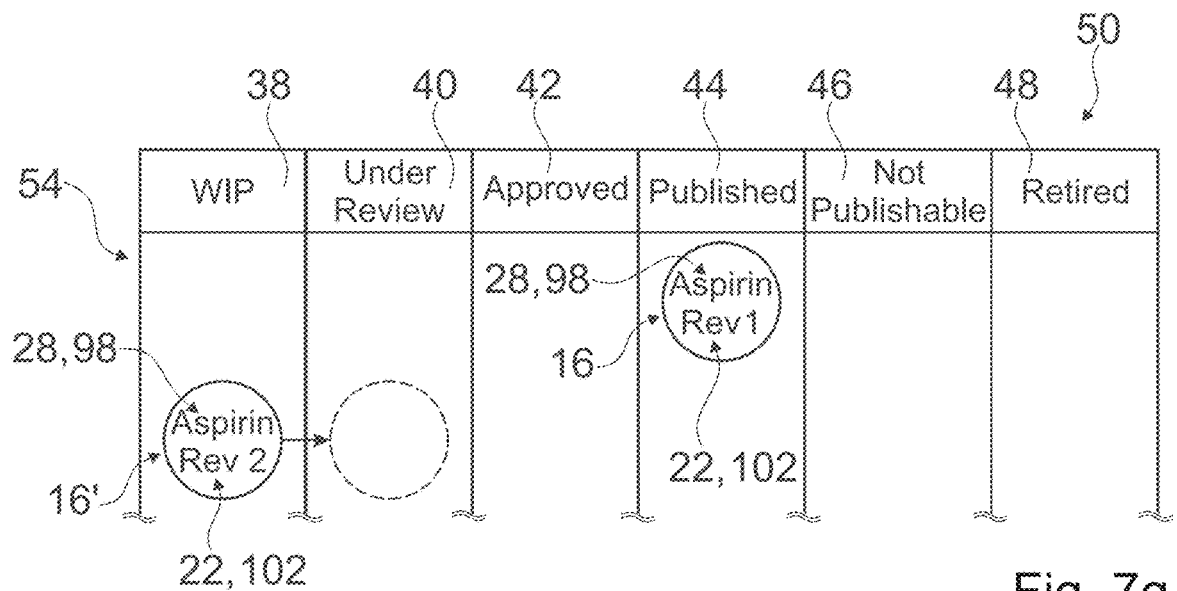
Figure 7H:
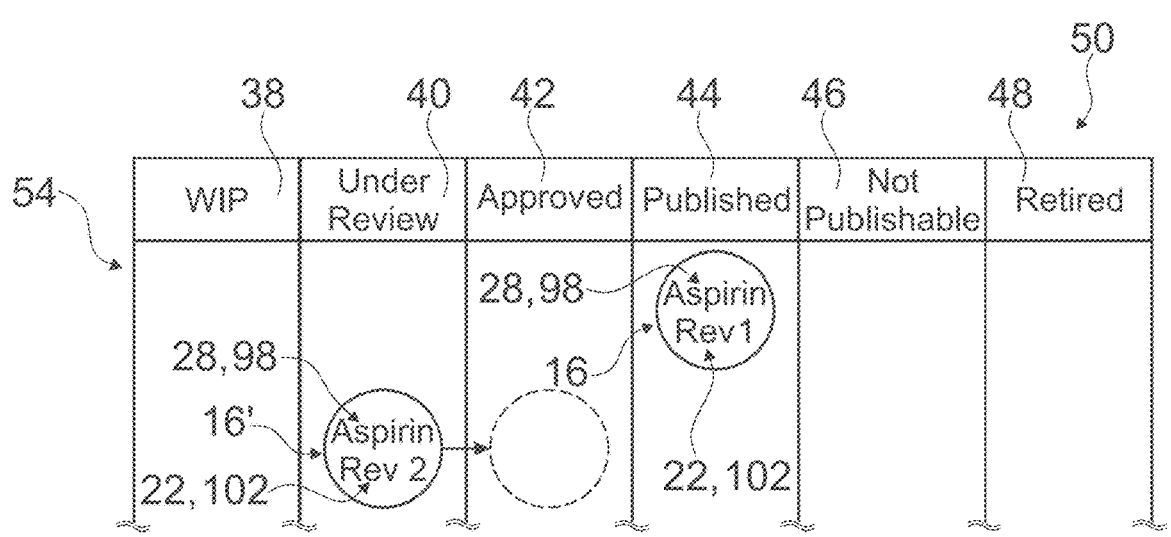
Figure 7I:
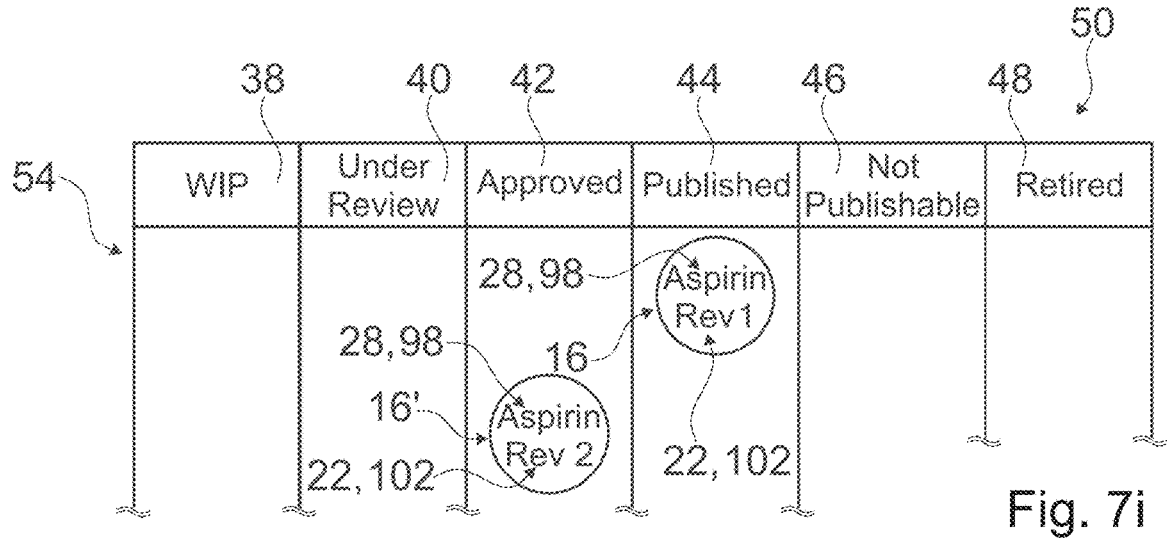
Figure 7J:
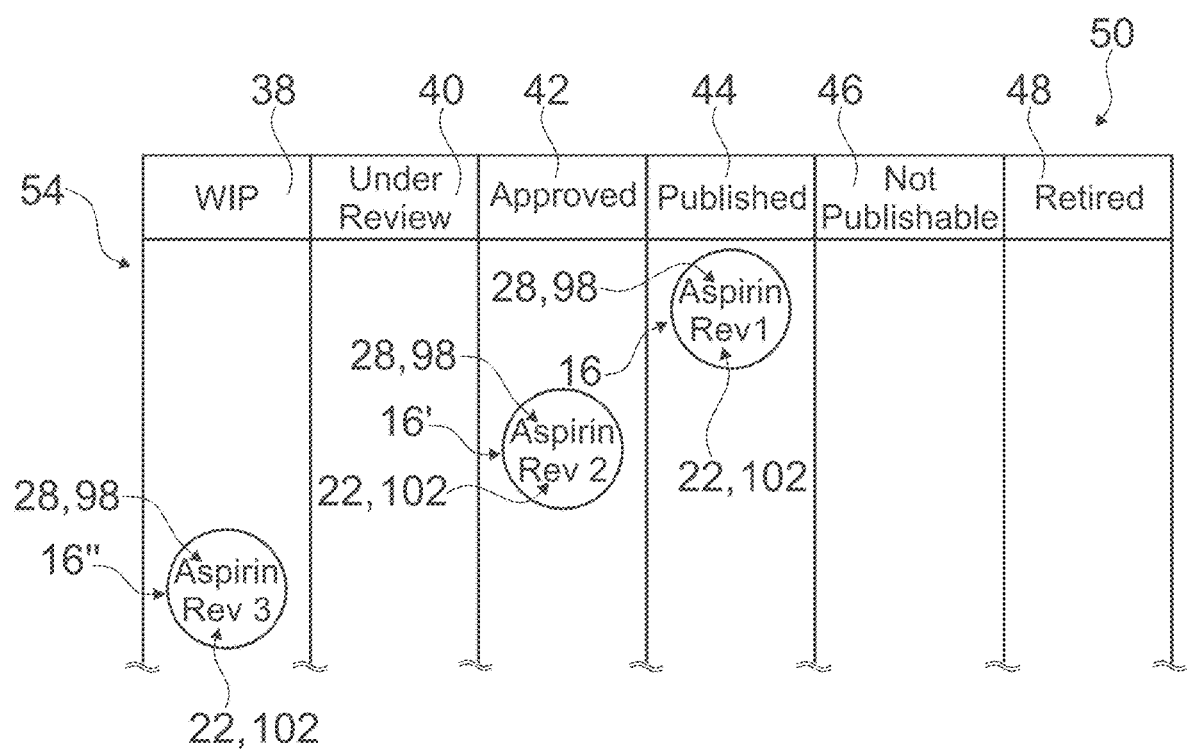
Figure 7K:
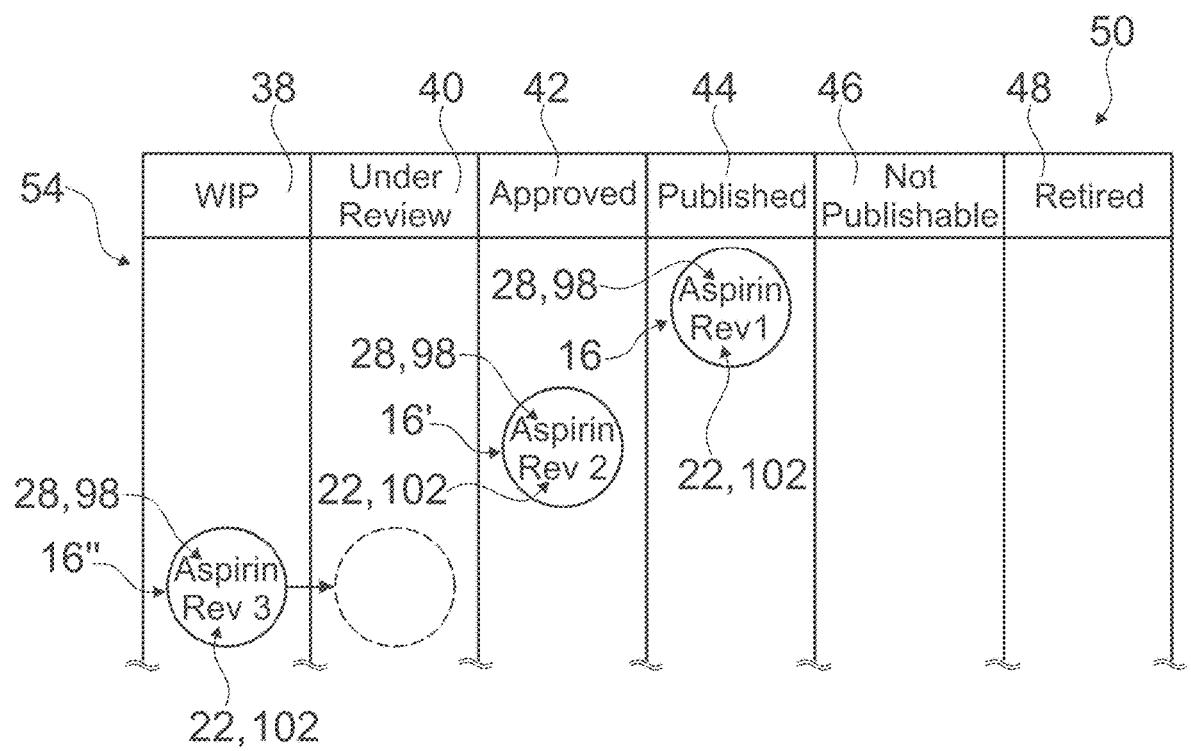
Figure 7L:
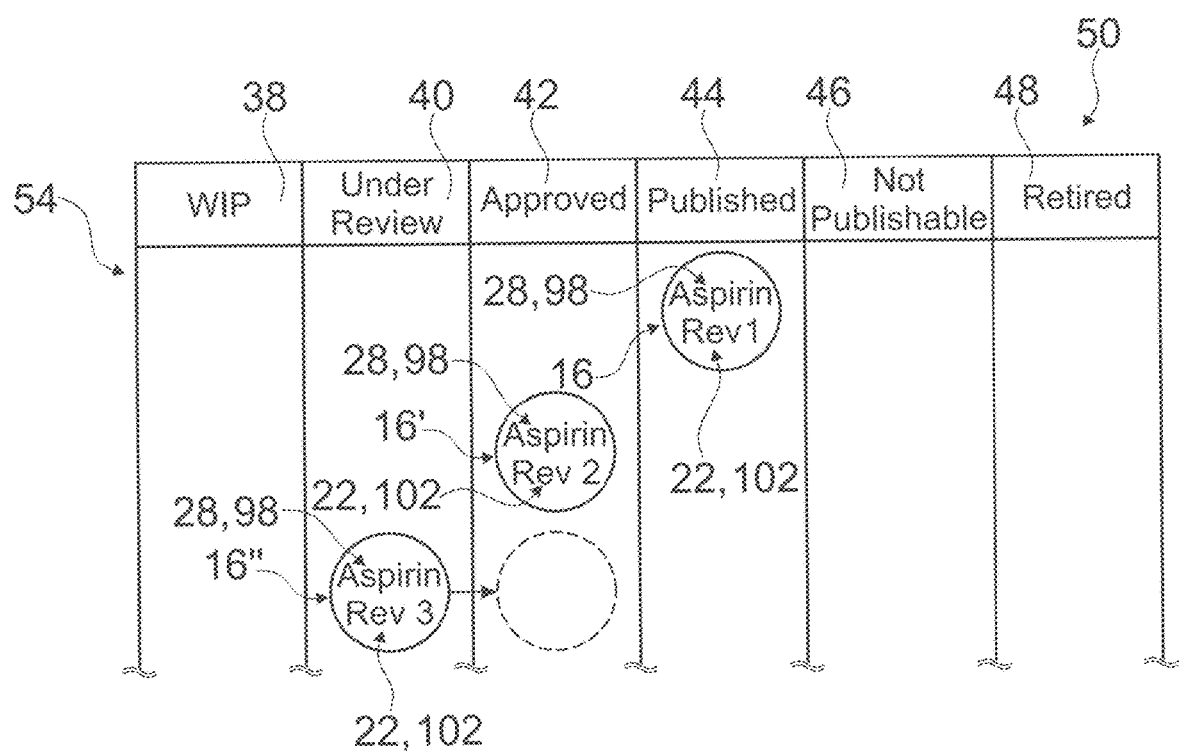
Figure 7M:
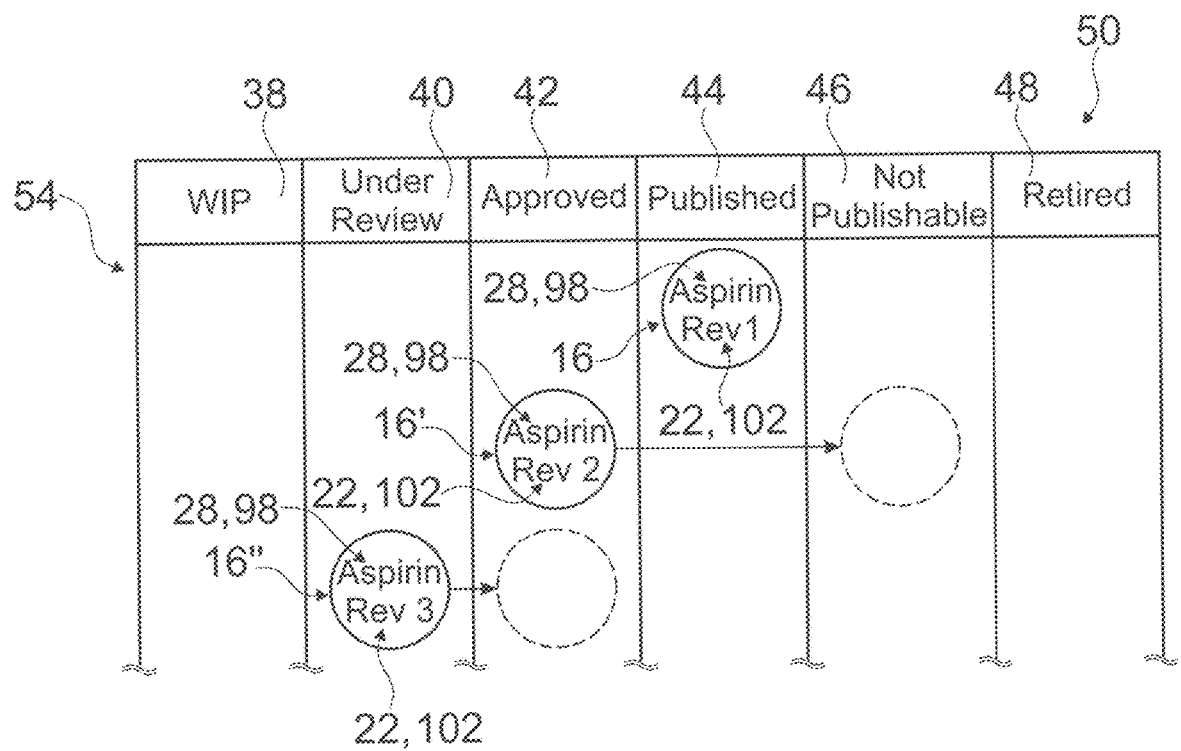
Figure 7N:
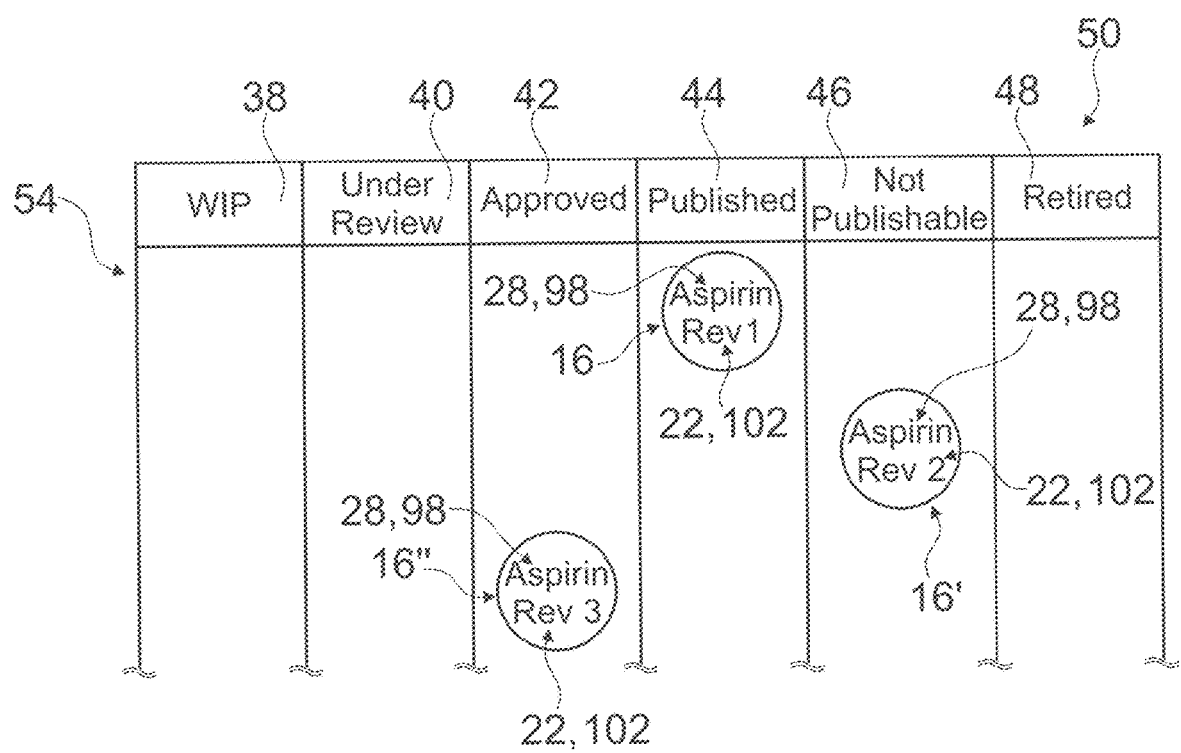
Figure 7O:
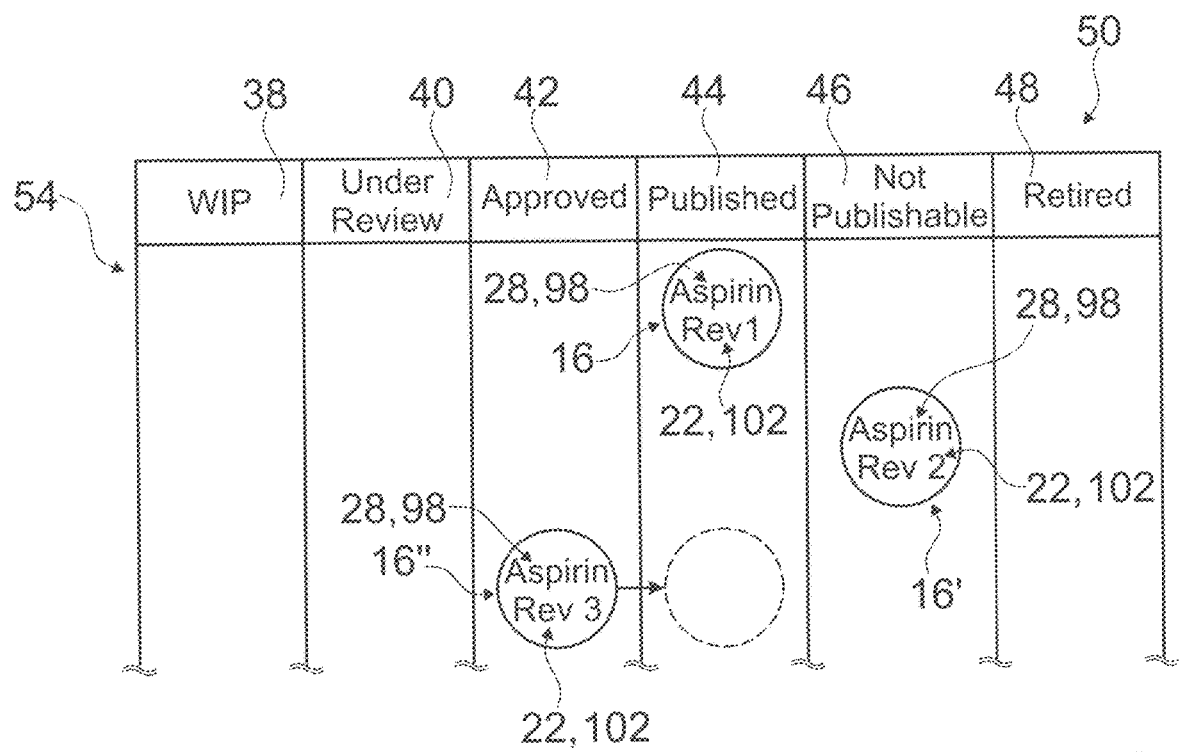
Figure 7P:
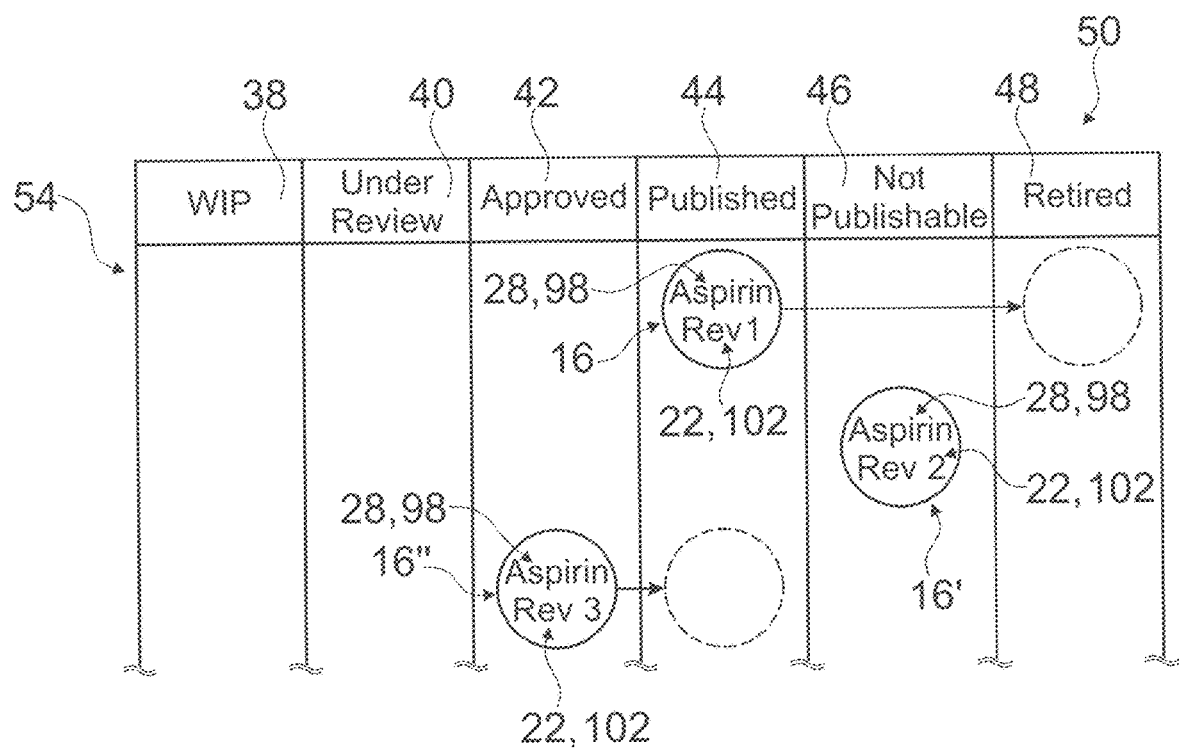
Figure 7Q:
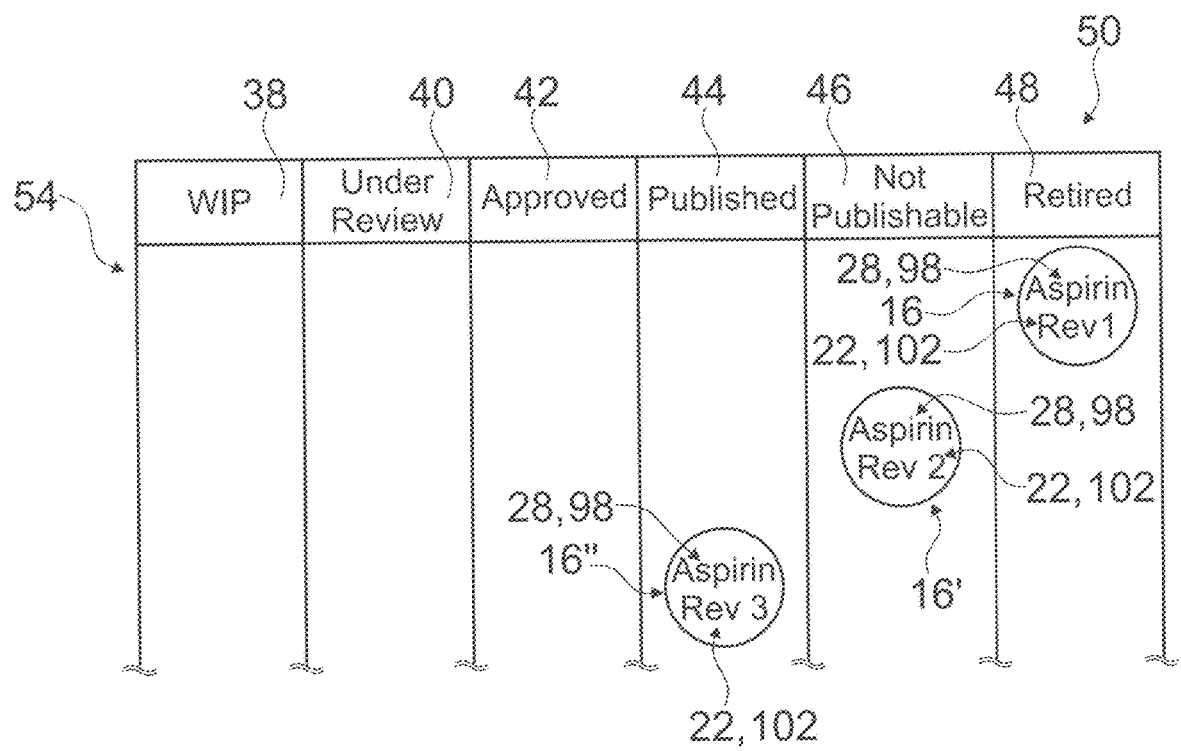
Figure 8:
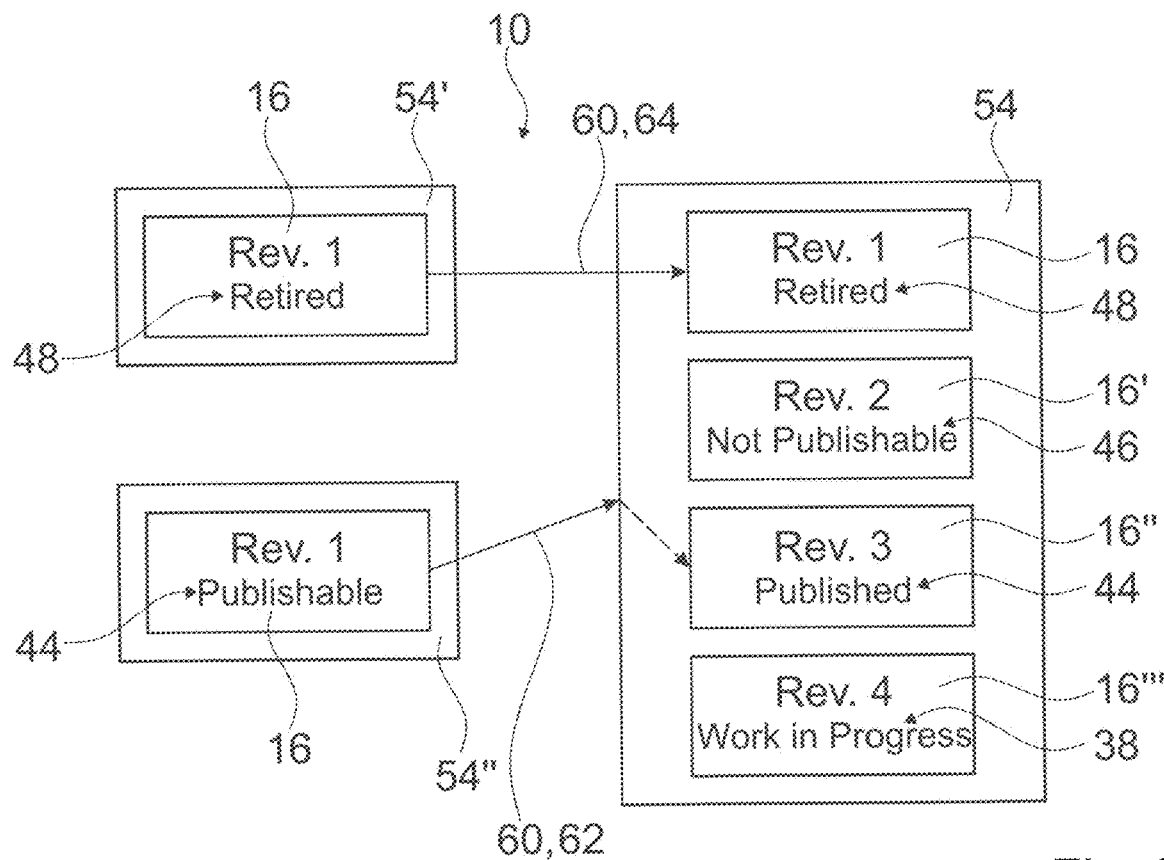
Figure 9A:
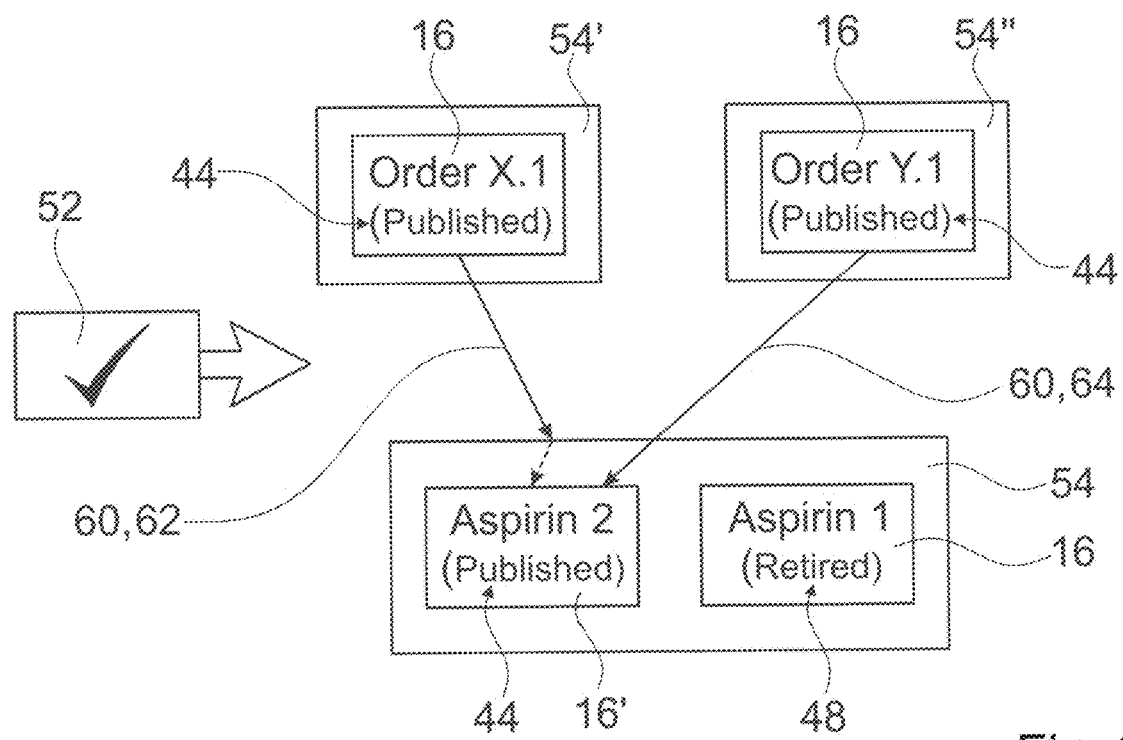
Figure 9B:
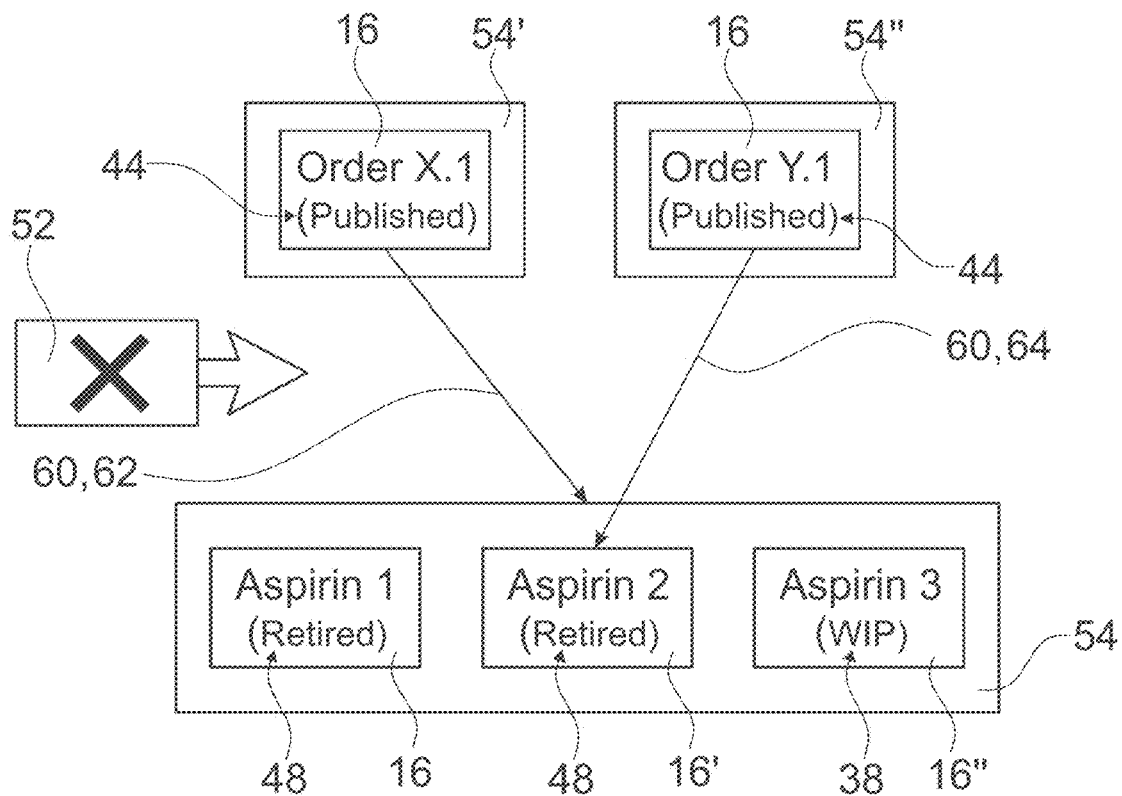
Figure 9C:
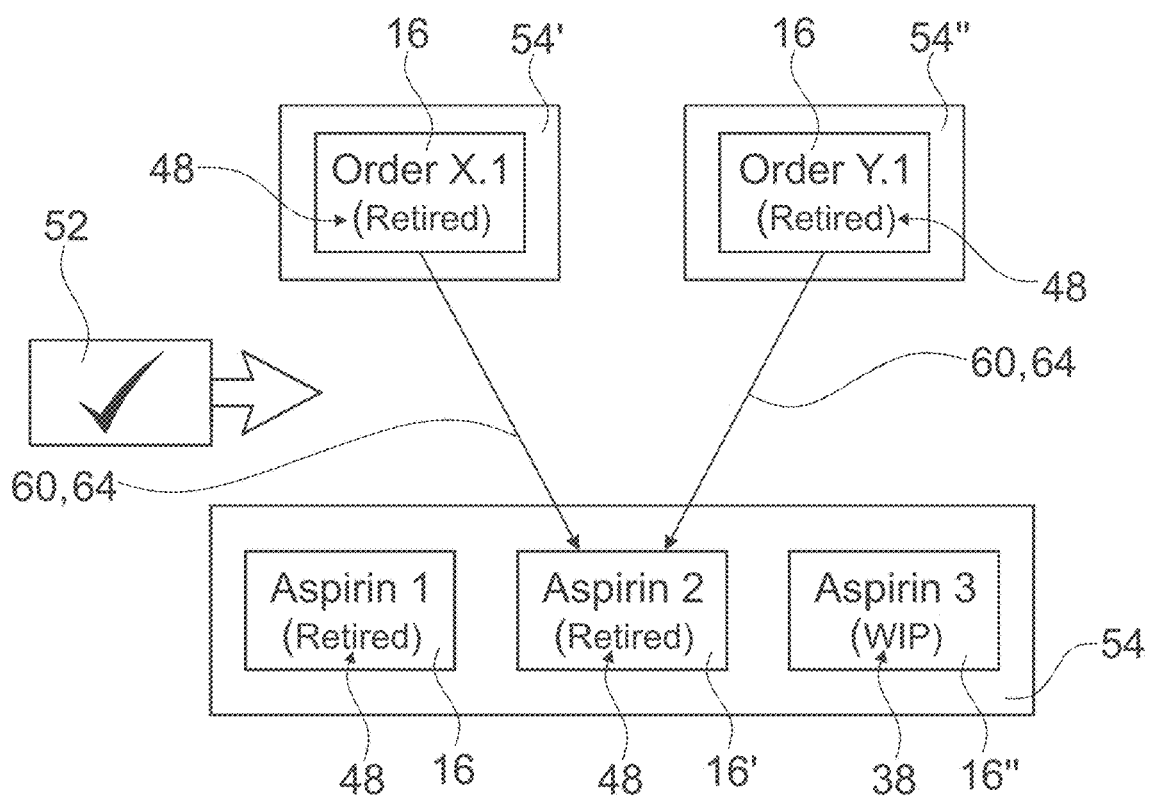
Figure 9D:
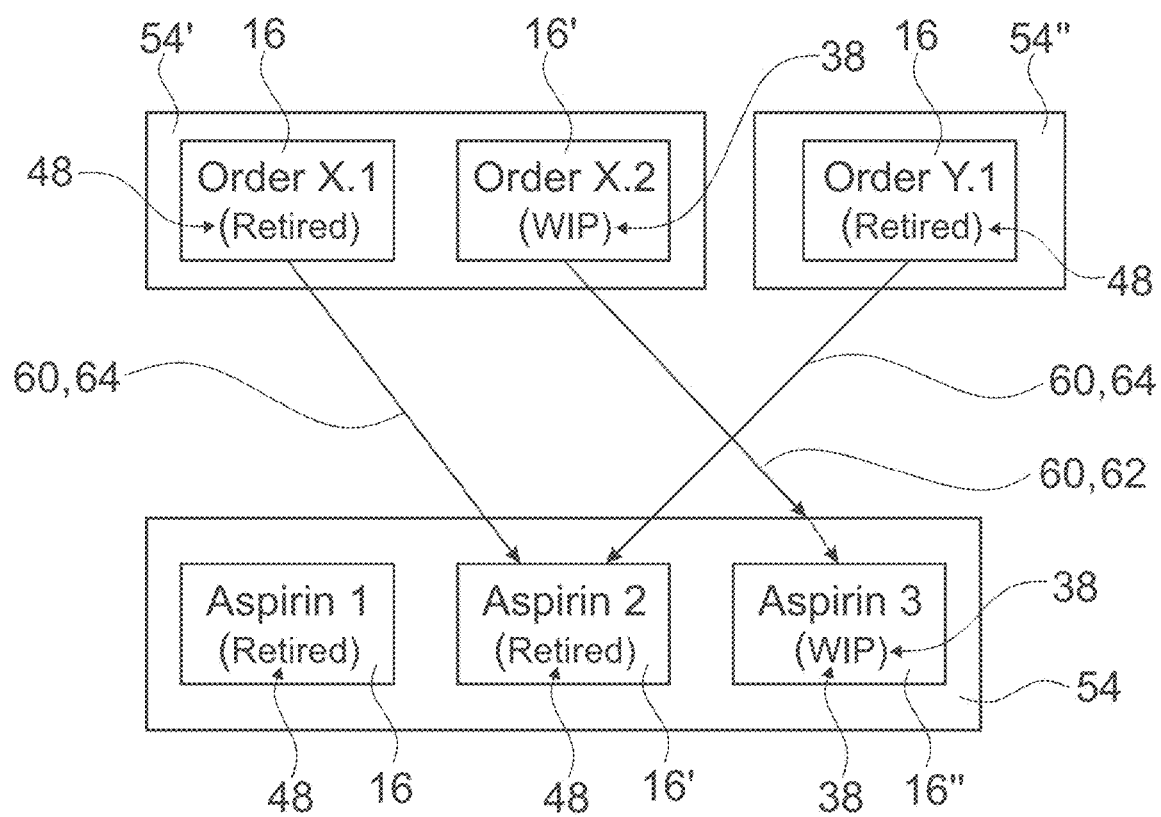
Figure 10:
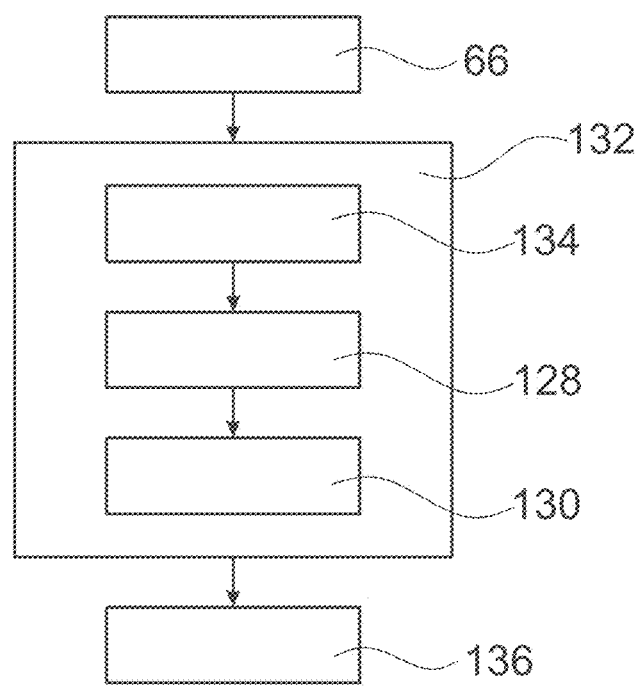

It is shown in:

FIG. 1 a schematic representation of a computer-implemented knowledge management platform system (KMPS), FIG. 2 a schematic representation of an architecture of the KMPS, FIG. 3 a schematic representation of the metamodel of the KMPS, FIG. 4 a schematic view of a knowledge management platform entity (KMPE) with multiple revisions of knowledge management platform items (KMPI), FIG. 5 shows a schematic example for a KMPE with two knowledge management platform designations (KMPD), FIG. 6 a schematic representation of a lifecycle transition schema of the KMPS, FIG. 7*a*-7*q* an exemplary illustration of revisions of KMPIs and associated lifecycle state transitions according to the lifecycle transition schema, FIG. 8 examples of knowledge management platform pointers (KMPP), like a generic KMPP and a revision-specific KMPP, FIG. 9*a*-9*d* an exemplary content evolution of the KMPS using the KMPPs, and FIG. 10 a schematic process diagram of a computer-implemented knowledge management method with the KMPS.

DESCRIPTION OF THE EXEMPLARY EMBODIMENTS

FIG. 1 shows a schematic representation of a computer-implemented knowledge management platform system (KMPS) 10. The KMPS 10 comprises a processor 12. The KMPS 10 comprises a non-transitory memory unit 14. The KMPS 10 comprises a repository 18. The repository 18 could be located/stored at least in part within the memory unit 14. The repository 18 could be located/stored at least in part within a (centralized or distributed) cloud computing and/or cloud storage system 72. The memory unit 14 is configured to include instructions which, when performed by the processor 16, induce an organization of knowledge management platform items (KMPI) 16, wherein the KMPIs 16 are allocated to knowledge management platform types (KMPT) 20 (for details see description and figures below) and wherein several consecutive instances, in particular revisions, of the KMPIs 16, 16', 16" are grouped within the repository 18, thereby forming a knowledge management platform entity (KMPE) 54. The KMPS 10 is configured to interact with one or more access and/or authoring devices 74. The access and/or authoring devices 74 can be implemented for example as personal computers, as mobile devices like smartphones, tablets or laptops. In addition, it is conceivable that the access and/or authoring devices 74 operate a Software-as-a-Service (SaaS) platform 76.

FIG. 2 shows a schematic representation of an architecture of the KMPS 10. The KMPS 10 comprises an authoring component 68. The authoring component 68 is implemented as an authoring workbench. The authoring component 68 is configured as an environment which allows authorized authors and/or creators 78 to read and, more importantly, to write data. The authoring component 68 is configured as an environment which allows authorized authors and/or creators 78 to create new KMPIs 16 and/or to revise KMPIs 16 of existing KMPEs 54. The authorized authors and/or creators 78 could, for example, be knowledge engineers. The KMPS 10 comprises a collaboration component 80. The collaboration component 80 is implemented as a collaboration workbench. The collaboration component 80 is configured as an environment which allows authorized collaborators 82 to read data and, more importantly, to comment on data. The authorized collaborators 82 could, for example, be subject matter experts. The collaboration component 80 is configured as an environment which allows authorized collaborators 82 to discuss and comment non-published KMPIs 16, this means for example newly created KMPIs 16 and/or currently revised KMPIs 16 of existing KMPEs 54. The KMPS 10 comprises a contributor web services/administration environment 84. The collaboration component 80 is embedded into the contributor web services/administration environment 84. The contributor web services/administration environment 84 provides a declarative content model. The contributor web services/administration environment 84 comprises an access control and permission management module 86. The access control and permission management module 86 is configured to check an identity of an author and/or creator 78 and/or of a collaborator 82. The identity check could for example comprise a verification via biometrical features and/or via a user-ID and a password. The access control and permission management module 86 comprises an authorization system which is highly flexible. In particular, nearly all kinds of permissions of the authorization system require a granting of permissions not only globally but for example also restricted to selected KMPTs 20 and/or limited to a creation of KMPIs 16/KMPEs 54 within a specific context or similar. For example, an author and/or creator 78 may be granted permission to only create order sets (KMPIs 16/KMPEs 54 of the KMPT 20 "order set"), but only if the order set KMPI 16/KMPE 54 is created in a "space" reserved for the company of the author and/or creator 78. Furthermore, it is also conceivable that other external sources 92 may contribute to the authoring component 68, the collaboration component 80 and/or to the contributor web services/administration environment 84 to some extent, in particular within set restrictions. Furthermore, it is also conceivable that the other external sources 92 may access the authoring component 68, the collaboration component 80 and/or to the contributor web services/administration environment 84 to some extent, in particular within set restrictions. Modifications to KMPIs 16, revisions of KMPIs 16, inactivation processes of KMPIs 16 and or creation processes of KMPIs 16 are tracked and secured via a blockchain. The external source 92 could be implemented as a blockchain security device. For example, the external source 92 could comprise at least parts of an audit log 122 of the blockchain. Alternatively or additionally, the audit log 122 could also be stored at least partly on site.

The KMPS 10 comprises a read-only component 70. The read-only component 70 is implemented as an end user portal. The read-only component 70 is configured as an environment which allows authorized end users 88 solely to read data. The read-only component 70 is configured as an environment which allows authorized end users 88 to access published KMPIs 16. The end users 88 could, for example, be medical professionals or hospital staff. The KMPS 10 comprises a consumer web services/administration environment 90. The read-only component 70 is embedded into the consumer web services/administration environment 90. The consumer web services/administration environment 90 provides a production content model. The consumer web services/administration environment 90 comprises the access control and permission management module 86. The access control and permission management module 86 is configured to check an identity of an end user 88. The identity check could for example comprise a verification via biometrical features and/or via a user-ID and a password. The production content model of the read-only component 70 is generated from the declarative content model of the authoring component 68 in a transformation procedure. In particular each new publishing of a KMPI 16 in the declarative content model triggers a transformation procedure deploying the newly published KMPI 16 into the production content model.

The KMPS 10 comprises an integrity checker module 52. The integrity checker module 52 is configured to check an integrity of a newly created KMPI 16. The integrity checker module 52 is configured to check an integrity of a newly revised KMPI 16. The integrity checker module 52 is configured to check an integrity of an existing KMPI 16 which was attributed with a new (changed) lifecycle state 38, 40, 42, 44, 46, 48. Upon detection of a violation of the integrity of such a KMPI 16, a storing of the newly created KMPI 16 within the repository 18 is prevented by the integrity checker module 52. Upon a detection of a violation of the integrity of such a KMPI 16, a change of the lifecycle state 38, 40, 42, 44, 46, 48 of the existing KMPI 16 is prevented. The non-transitory memory unit 14, in particular the integrity checker module 52, contains at least one validation rule 118, 118', 118", which is executed by the processor 12 during an integrity check by the integrity checker module 52 and based upon which a violation of the integrity of a KMPI 16 can be detected. The validation rules 118, 118', 118" are (completely) customizable. Each customization of a validation rule 118, 118', 118" itself is stored as a KMPI 16. A specific KMPT 20, in particular a "validation rule" KMPT 120, is allocated to each of said KMPIs 16 containing at least one validation rule 118, 118', 118". The integrity checker module 52 comprises an inference unit 56. The inference unit 56 is implemented as a semantic inference unit. Alternatively or additionally, the inference unit 56 could also be implemented as a structural inference unit. The inference unit 56 is configured to evaluate logical expressions within a KMPI 16. The inference unit 56 is configured to evaluate logical expressions within a set of KMPIs 16. The inference unit 56 is configured to evaluate logical expressions within the whole repository 18. The inference unit 56 is configured to link a KMPI 16 with other KMPIs 16 and/or with attributes or metadata of the KMPIs 16.

FIG. 3 shows a schematic representation of the metamodel, in particular the meta-modeled structure, of the KMPS 10. The metamodel, in particular the meta-modeled structure is stored within the memory unit 14. The meta-modeled structure of the KMPS 10 forms an object model. The meta-modeled structure of the KMPS 10 constitutes an ontology model. The meta-modeled structure of the KMPS 10 organizes the KMPIs 16. The meta-modeled structure of the KMPS 10 organizes the KMPEs 54. The meta-modeled structure of the KMPS 10 organizes the KMPTs 20. The meta-modeled structure is completely self-referential. The KMPTs 20 are components of the meta-modeled structure. The KMPIs 16 and/or the KMPEs 54 are allocated to KMPTs 20. Each KMPT 20 is customizable. Each customization of a KMPT 20 (each customized KMPT 124) itself is stored as a KMPI 16. Each customized KMPT 124 inherits at least all non-customized properties of a bequeathing KMPT 20. Preferably, each customized KMPT 124 further inherits all customized properties of the bequeathing KMPT 20.

Some of the KMPTs 20 are implemented as core KMPTs 22, 24, 26, 28, 30. Each core KMPT 22, 24, 26, 28, 30 defines an essential group of properties. Each of the essential group of properties must be attributed to each KMPI 16. A first core KMPT 24 defines a first essential group of properties, which defines identities 94, 94', 94" of KMPIs 16. Each identity 94, 94', 94" is itself stored within the repository 18 as a KMPI 16. In addition, the first core KMPT 24 defines an essential group of properties, which defines a revision number 102 of an instance and/or a revision of a KMPI 16. Each revision number 102 is itself stored within the repository 18 as a KMPI 16. A second essential group of properties of a second core KMPT 22 defines the lifecycle states 38, 40, 42, 44, 46, 48. Each lifecycle state 38, 40, 42, 44, 46, 48 is itself stored within the repository 18 as a KMPI 16. The KMPIs 16 which are defined as lifecycle states 38, 40, 42, 44, 46, 48 include at least one instruction which is to be considered when another KMPI 16 attributed with a respective lifecycle state 38, 40, 42, 44, 46, 48 and stored within the repository 18 is organized by the processor 12 according to instructions stored within the non-transitory memory unit 14. A third core KMPT 26 defines a third essential group of properties, which defines provenances 96, 96', 96" of each KMPI 16. Each provenance 96, 96', 96" is itself stored within the repository 18 as a KMPI 16. In addition, the third core KMPT 26 defines an essential group of properties, which defines an author- and/or creator-identity 104, 104', 104" (or a curator identity) of a KMPI 16. Each author and/or creator identity 104, 104', 104" is itself stored within the repository 18 as a KMPI 16. In addition, the third core KMPT 26 defines an essential group of properties, which defines a date 106, 106', 106" of a KMPI 16. Each date 106, 106', 106" is itself stored within the repository 18 as a KMPI 16. In addition, the third core KMPT 26 comprises an essential group of properties, which defines a source 110, 110', 110" of a content of a KMPI 16. Each source 110, 110', 110" is itself stored within the repository 18 as a KMPI 16. A fourth core KMPT 28 defines a fourth essential group of properties, which defines the various names 98, 98', 98" that can be assigned to each KMPI 16. Each name 98, 98', 98" is itself stored within the repository 18 as a KMPI 16. A fifth core KMPT 30 defines a fifth essential group of properties, which defines a context 100, 100', 100" of each KMPI 16. Each context 100, 100', 100" is itself stored within the repository 18 as a KMPI 16.

The KMPS 10, in particular the meta-modeled structure of the KMPS 10, comprises at least one knowledge management platform designation (KMPD) 58. Each KMPD 58 is stored within the repository 18 as a KMPI 16. Each KMPD 58 is attributed to at least one KMPI 16, in particular to at least one KMPE 54. Each KMPD 58 has at least one designation type 112, 114, 116. A first exemplary designation type 112 is implemented as a name. A second exemplary designation type 114 is implemented as a code. A third exemplary designation type 116 is implemented as a symbol. A total number of KMPDs 58 which are attributable to each KMPI 16, in particular each KMPE 54, is unlimited.

FIG. 4 shows a schematic view of a KMPE 54 with multiple revisions. The KMPE 54 comprises several KMPIs 16, in particular several revisions of KMPIs 16, 16', 16", 16''', 16''''. Each revision of the KMPIs 16, 16', 16", 16''', 16'''' is attributed with a lifecycle state 38, 40, 42, 44, 46, 48. The lifecycle states 38, 40, 42, 44, 46, 48 comprise terminal lifecycle states 46, 48. The lifecycle states 38, 40, 42, 44, 46, 48 comprise non-terminal lifecycle states 38, 40, 42, 44. In the example of FIG. 4 a first revision of the KMPI 16 is attributed with a "retired" lifecycle state 46. The "retired" lifecycle state 46 is a terminal lifecycle state. In the example of FIG. 4, a second revision of the KMPI 16' is attributed with a "published" lifecycle state 44. The "published" lifecycle state 44 is a non-terminal lifecycle state. In the example of FIG. 4 a third revision of the KMPI 16" and a fourth revision of the KMPI 16''' are attributed with a "not publishable" lifecycle state 48. The "not publishable" lifecycle state 48 is a terminal lifecycle state. In the example of FIG. 4, a fifth revision of the KMPI 16'''' is attributed with a "work-in-progress" lifecycle state 38. The "work-in-progress" lifecycle state 38 is a non-terminal lifecycle state. At least two more non-terminal lifecycle states, which are not shown in FIG. 4, may exist, the "under review" lifecycle state 40 and the "approved" lifecycle state 42. The several KMPIs 16, 16', 16", 16''', 16'''' of the KMPE 54 all comprise the same KMPT 20. The several KMPIs 16, 16', 16", 16''', 16'''' of the KMPE 54 all comprise the same core KMPT 22, 24, 26, 28, 30. The several KMPIs 16, 16', 16", 16''', 16'''' of the KMPE 54 all comprise the same KMPD 58, in particular the same designation types 112, 114, 116. The several KMPIs 16, 16', 16", 16''', 16'''' of the KMPE 54 may have different content information, i.e. they may contain different knowledge. FIG. 5 shows an example for a KMPE 54 with two KMPDs 58.

FIG. 6 shows a schematic representation of a lifecycle transition schema 50 of the KMPS 10. The KMPS 10 comprises the lifecycle transition schema 50. The lifecycle transition schema 50 is stored within the memory unit 14. The lifecycle transition schema 50 is implemented by the ensemble of all available lifecycle states 38, 40, 42, 44, 46, 48. The lifecycle transition schema 50 at least defines accessibility pathways for the KMPS 10 when accessing a KMPE 54. The lifecycle transition schema 50 itself is stored as a KMPI 16, preferably within the repository 18. The lifecycle transition schema 50 is customizable. A plurality of lifecycle transition schemas 50 can exist simultaneously, in particular for KMPIs 16 attributed with different KMPTs 20. The lifecycle transition schema 50 governs an "order" (precedence) 126 of the lifecycle states 38, 40, 42, 44, 46, 48. The "lowest order" (lowest precedence) lifecycle states are the terminal lifecycle states 46, 48. The "highest order" (highest precedence) lifecycle state is the "published" lifecycle state 44. The "second highest order" (second highest precedence) lifecycle state is the "approved" lifecycle state 42. The "third highest order" (third highest precedence) lifecycle state is the "under review" lifecycle state 40. The "fourth highest order" (fourth highest precedence) lifecycle state is the "work-in-progress" lifecycle state 38. The KMPIs 16 with the "published" lifecycle state 44 are visible to the end user 88, searchable by the end user 88 and/or queryable by the end user 88, in particular by means of the read-only component 70. All KMPIs 16 with other lifecycle states than the "published" lifecycle state 44 are only visible/accessible via the authoring component 68. It is conceivable that in an advanced mode (e.g. by an advanced search query) also KMPIs 16 with the "under review" lifecycle state 40 and/or KMPIs 16 with the "approved" lifecycle state 42 are accessible at least for some end users 88 via the read-only component 70. On the other hand, it is also conceivable that the KMPIs 16 with the "under review" lifecycle state 40 and/or KMPIs 16 with the "approved" lifecycle state 42 are accessible at least for some end users 88 via the read-only component 70 only via simple searches but not via advanced search queries. The lifecycle state 38, 40, 42, 44, 46, 48 of a KMPI 16 with a terminal lifecycle state 46, 48 is immutable, except for transitions into another terminal lifecycle state 46, 48. The lifecycle state 38, 40, 42, 44, 46, 48 of a KMPI 16 with a non-terminal lifecycle state 38, 40, 42, 44 is mutable into a "higher order" (higher precedence) lifecycle state 40, 42, 44 or into a terminal lifecycle state 46, 48. The "work-in-progress" lifecycle state 38 is mutable into the "under review" lifecycle state 40 or into the "not publishable" lifecycle state 46. Other lifecycle state transitions of the "work-in-progress" lifecycle state 38 are not allowed. The "under review" lifecycle state 40 is mutable into the "approved" lifecycle state 42 or into the "not publishable" lifecycle state 46. Other lifecycle state transitions of the "under review" lifecycle state 38 are not allowed. The "approved" lifecycle state 42 is mutable into the "published" lifecycle state 44 or into the "not publishable" lifecycle state 46. Other lifecycle state transitions of the "approved" lifecycle state 42 are not allowed. The "published" lifecycle state 44 is only mutable into the "retired" lifecycle state 48. Other lifecycle state transitions of the "published" lifecycle state 44 are not allowed.

KMPIs 16 with a non-terminal lifecycle state 38, 40, 42, 44 within the repository 18 are revisable. KMPIs 16 with a terminal lifecycle state 46, 48 within the repository 18 are not revisable. Alternatively, also KMPIs 16 with a terminal lifecycle state 46, 48 within the repository 18 could be revisable. Upon a revision of a revisable KMPI 16, in particular a KMPI 16 with a non-terminal lifecycle state 46, 48, a new instance and/or a revision of the KMPI 16' with a newly attributed lifecycle state 38, 40, 42, 44, 46, 48 is created and stored within the repository 18. The new instance of the KMPI 16' or the new revision of the KMPI 16', which was created and stored upon revision of the KMPI 16, is always automatically attributed a non-terminal "initial" lifecycle state, in particular the "work-in-progress" lifecycle state 38. The non-transitory memory unit 14 contains instructions which, when performed by the processor 12 during organizing of the repository 18, prevent a modification of the KMPIs 16 (except for attributed metadata) unless the "work-in-progress" lifecycle state 38 is attributed to the KMPIs 16 to be modified. An execution of at least one checking procedure (validation rule 118) of the integrity checker module 52 for a specific KMPI 16 depends on the lifecycle state 38, 40, 42, 44, 46, 48 of said KMPI 16. Some checking procedures (validation rules 118) of the integrity checker module 52 are not performed on KMPIs 16 with a "work-in-progress" lifecycle state 38.

At least the "published" lifecycle state 44 is only attributable to one single KMPI 16 of a KMPE 54 within the repository 18 at one time. Preferably each non-terminal lifecycle state 38, 40, 42, 44 is only attributable to one single KMPI 16 of a KMPE 54 within the repository 18 at one time. The terminal lifecycle states 46, 48 are attributable to several different KMPIs 16 of a KMPE 54 at the same time. A lifecycle state 38, 40, 42, 44, 46, 48 of a first KMPI 16 having a non-terminal lifecycle state 38, 40, 42, 44 and belonging to a KMPE 54 is automatically changed into a terminal lifecycle state 46, 48 when a second KMPI 16' belonging to the same KMPE 54 is attributed a "new" non-terminal lifecycle state 38, 40, 42, 44 48, which is identical to the non-terminal lifecycle state 38, 40, 42, 44 of the first KMPI 16.

FIGS. 7a to 7q exemplarily illustrate such revisions of KMPI and associated lifecycle state transitions according to the lifecycle transition schema 50 described above. In FIG. 7a, the KMPE 54 comprises only one first KMPI 16. The first KMPI 16 comprises a fourth core KMPT 28 defining a name 98 "Aspirin". The first KMPI 16 comprises a first core KMPT 22 defining a revision number 102 "Rev 1". The KMPE 54 with the first KMPI 16 has recently been created within the authoring workbench and therefore the first KMPI 16 is attributed with the "work-in-progress" lifecycle state 38. When the author and/or creator 78 has completed the creation of the first KMPI 16 (e.g. the author and/or creator 78 has filled in all relevant knowledge into the first KMPI 16), the "under review" lifecycle state 40 is attributed to the first KMPI 16 (see FIG. 7b). KMPIs 16 with the "under review" lifecycle state 40 are accessible for review and commenting by collaborators 82 and/or authors/creators 78 via the authoring component 68 and/or via the collaboration component 80. When the authors/creators 78 and/or collaborators 82 have completed the review process, the first KMPI 16 is attributed with the "approved" lifecycle state 42 in case the collaborators 82 and/or authors/creators 78 approve the first KMPI 16, in particular the content of the first KMPI 16 (see FIG. 7c). KMPIs 16 with the "approved" lifecycle state 42 are ready to be published. It is conceivable that a curator of the KMPS 10 is entrusted with the final decision to publish a KMPI 16 (see FIG. 7d). When the "published" lifecycle state 44 is attributed to the first KMPI 16, the first KMPI 16 is accessible to regular end users 88 via the read-only component 70, in particular via the end user portal (see FIG. 7e).

In FIG. 7f, the KMPE 54 comprises the first KMPI 16 and a second KMPI 16'. The second KMPI 16' represents a revision of the first KMPI 16. The second KMPI 16' comprises a fourth core KMPT 28 defining a name 98 "Aspirin". The second KMPI 16' comprises a first core KMPT 22 defining a revision number 102 "Rev 2". The KMPE 54 with the second KMPI 16' is created after the first KMPI 16, in particular after the first KMPI 16 is published. The second KMPI 16' is created within the authoring workbench and therefore the second KMPI 16' is attributed with the "work-in-progress" lifecycle state 38. The two KMPIs 16, 16' exist in parallel and are both part of one single KMPE 54 (see FIG. 7f). The second KMPI 16' undergoes the same review and approval process as the first KMPI 16 until it reaches the "approved" lifecycle state 42 (see FIGS. 7g to 7i). During the whole process until the second KMPI 16' reaches the "approved" lifecycle state 42, the first KMPI 16 and its attributed "published" lifecycle state 44 are unaffected.

In FIG. 7j, the KMPE 54 comprises the first KMPI 16, a second KMPI 16' and a third KMPI 16". The third KMPI 16" represents a further revision of the first KMPI 16 or of the second KMPI 16'. The third KMPI 16" comprises a fourth core KMPT 28 defining a name 98 "Aspirin". The third KMPI 16" comprises a first core KMPT 22 defining a revision number 102 "Rev 3". The KMPE 54 with the third KMPI 16' is created after the first KMPI 16 and after the second KMPI 16', in particular after the first KMPI 16 is published and after the second KMPI 16' is approved or put under review. The third KMPI 16" is created within the authoring workbench and therefore the third KMPI 16" is attributed with the "work-in-progress" lifecycle state 38. The three KMPIs 16, 16', 16" exist in parallel and are all three part of one single KMPE 54 (see FIG. 7j). The third KMPI 16" undergoes the same creation process as the first KMPI 16 and the second KMPI 16' until it reaches the "under review" lifecycle state 40 (see FIGS. 7k and 7l). During the whole process until the third KMPI 16" reaches the "under review" lifecycle state 40, the first KMPI 16 and its attributed "published" lifecycle state 44 and the second KMPI 16' and its "approved" lifecycle state 42 are unaffected.

In FIG. 7m, the third KMPI 16" is approved via the authoring component 68 and/or the collaboration component 80 of the KMPS 10. Consequently, the "approved" lifecycle state 42 is allocated to the third KMPI 16" of the KMPE 54. The "approved" lifecycle state 42 is only attributable to one single KMPI 16, 16' 16" of a KMPE 54 within the repository 18 at one time. Thus, the lifecycle state 42 of the second KMPI 16', having the "approved" lifecycle state 42 until now and belonging to the KMPE 54, is automatically changed into a terminal lifecycle state 46, in particular to the "not publishable" lifecycle state 46 because it is not yet published, when the third KMPI 16", which belongs to the same KMPE 54, is attributed the "approved" lifecycle state 42 (see FIG. 7n). In FIG. 7o, the third KMPI 16" is published. Consequently, the "published" lifecycle state 44 is allocated to the third KMPI 16" of the KMPE 54. The "published" lifecycle state 44 is only attributable to one single KMPI 16, 16' 16" of a KMPE 54 within the repository 18 one time. Thus, the lifecycle state 44 of the first KMPI 16, having the "published" lifecycle state 44 until now and belonging to the KMPE 54, is automatically changed into a terminal lifecycle state 48, in particular the "retired" lifecycle state 46, because it was published before, when the third KMPI 16", which belongs to the same KMPE 54 is attributed the "published" lifecycle state 44 (see FIG. 7p). In FIG. 7q only the third KMPI 16" of the KMPE 54 still has a non-terminal lifecycle state 44, namely the "published" lifecycle state, and thus is readable for the end user 88. The second KMPI 16' and the first KMPI 16 are both attributed with a terminal lifecycle state 46, 48 and thus are not visible to the end user 88 (except for historical or traceability purposes, if applicable).

The non-transitory memory unit 14 is configured to store knowledge management platform pointers (KMPP) 60 (see also FIGS. 8 to 9d). The KMPS 10 comprises the KMPPs 60. Each KMPP 60 is stored as a KMPI 16 within the repository 18 itself. Each of the KMPP 60 is assignable to at least one KMPI 16 of a KMPE 54. A KMPP 60 is configured to at least link the at least one KMPI 16 of the KMPE 54 with at least one further target KMPE 54', 54" within the repository 18. Alternatively or additionally, the KMPP 60 is configured to at least link the at least one KMPI 16 of the KMPE 54 with at least one other KMPI 16' of a further KMPE 54', 54" within the repository 18. The lifecycle state 38, 40, 42, 44, 46, 48 of a KMPI 16 within the repository 18 defines if a connection and/or a linking of the KMPI 16 to another KMPI 16' (or KMPE 54', 54") within the repository 18 is permitted or not. The KMPS 10 comprises two different groups of KMPPs 60. A first group of KMPPs 60 is implemented as generic KMPPs 62. A second group of KMPPs 60 is implemented as revision-specific KMPPs 64. A KMPP 60, 62, 64 assigned to a KMPI 16 of a KMPE 54 is only permitted to point to other KMPEs 54 with compatible lifecycle states 38, 40, 42, 44, 46, 48. FIG. 8 shows examples of a generic KMPP 62 and a revision-specific KMPP 64. The example of FIG. 8 shows a first KMPE 54, a second KMPE 54', and a third KMPE 54". The first KMPE 54 comprises four KMPIs 16, 16', 16", 16''', of which the first KMPI 16 represents a first revision and has the "retired" lifecycle state 48, the second KMPI 16' represents a second revision and has the "not publishable" lifecycle state 46, the third KMPI 16" represents a third revision and has the "published" lifecycle state 44 and the fourth KMPI 16''' represents a fourth revision and has the "work-in-progress" lifecycle state 38. The second KMPE 54' and the third KMPE 54" comprise only one KMPI 16 each. The only KMPI 16 of the second KMPE 54' has the "retired" lifecycle state 48. The only KMPI 16 of the third KMPE 54 has the "published" lifecycle state 44. The second KMPE 54' is connected to the first KMPE 54 via a revision-specific KMPP 64. The revision-specific KMPP 64 is configured to always point to a specific KMPI 16 of a target KMPE 54, in particular even after a revision of the target KMPE 54. In the example of FIG. 8, the revision-specific KMPP 64 connecting the second KMPE 54' with the first KMPE 54 points directly to the first revision of the first KMPE 60, namely the first KMPI 16 of the first KMPE 54. The third KMPE 54" is connected to the first KMPE 54 via a generic KMPP 62. The generic KMPP 62 is configured to always point to the KMPI 16 of a target KMPE 54 which has the highest order non-terminal lifecycle state 38, 40, 42, 44 of all KMPIs 16 within the KMPE 54. Preferably, a generic KMPP 62 is configured to always point to the KMPI 16 of a target KMPE 54 which is attributed with the "published" lifecycle state 44. If any change in the lifecycle states 38, 40, 42, 44 of the KMPIs 16 of the target KMPE 54 is detected (e.g. upon detection of at least one revision of a KMPI 16 of the target KMPE 54), the KMPS 10 induces an automatic updating of each generic KMPP 62 pointing to the target KMPE 54. If, for example after a change in the KMPE 54, a different KMPI 16 of the KMPE 54 is attributed with the "published" lifecycle state 44 than before the change, the automatic updating changes the targets of all generic KMPP 62 pointing to the target KMPE 54 from the KMPI 16 of the target KMPE 54 which was attributed the "published" lifecycle state 44 before the change to the KMPI 16 of the target KMPE 54 which is attributed the "published" lifecycle state after the change.

FIGS. 9a to 9d show an exemplary content evolution (and an evolution of connections) of the KMPS 10 with the KMPP 60. In FIG. 9a an exemplary initial state of a KMPS 10 is displayed. The KMPS 10 comprises a first KMPE 54, a second KMPE 54' and a third KMPE 54". The first KMPE 54 comprises a first revision of a KMPI 16 with a "retired" lifecycle state 48 and a second KMPI 16' with a "published" lifecycle state 44. The second KMPE 54' and the third KMPE 54" each comprise only one KMPI 16, both having the "published" lifecycle state 44. The second KMPE 54' and the first KMPE 54 are connected via a KMPP 60, which is implemented as a generic KMPP 62. The KMPI 16 of the second KMPE 54' is connected to the first KMPE 54 via the generic KMPP 62. The third KMPE 54" and the first KMPE 54 are connected via a KMPP 60, which is implemented as a revision-specific KMPP 64. The KMPI 16 of the third KMPE 54" is connected to the first KMPE 54, more precisely to the second KMPI 16' of the first KMPE 54, via the revision-specific KMPP 64. The lifecycle state 38, 40, 42, 44, 46, 48 of the KMPIs 16 within the repository 18 define whether an assignment of a specific KMPP 60, 62, 64 to the KMPIs 16 and/or a pointing of the specific KMPP 60, 62, 64 to target KMPIs 16 and/or to target KMPEs 54 is permitted or not. A KMPP 60, 62, 64 assigned to a KMPI 16 of a KMPE 54 is only permitted to point to other KMPEs 54 with compatible lifecycle states 38, 40, 42, 44, 46, 48. The integrity checker module 52 is configured to automatically check an integrity of the connections of the KMPP 60.

In FIG. 9b the second KMPI 16' of the first KMPE 54 is retired, i.e. the lifecycle state of the second KMPI 16' has changed into the "retired" lifecycle state 48. Furthermore, a third KMPI 16" is newly created within the first KMPE 54 and automatically attributed with the "work-in-progress" lifecycle state 38. Consequently, the revision-specific KMPP 64 connecting the third KMPE 54" with the second KMPI 16' of the first KMPE 54 points to a KMPI 16' with the "retired" lifecycle state 48. Since a connection between a KMPI 16 with a "published" lifecycle state 44 and a KMPI 16 with a "retired" lifecycle state 48 is invalid, the integrity checker module 52 will prohibit this change and/or send out an invalidity warning. In addition, the generic KMPP 62 connecting the second KMPE 54' with the first KMPE 54 now misses a valid target, since the KMPI 16 of the first KMPE 54 with its "highest order" (highest precedence) non-terminal lifecycle state only has the "work-in-progress" lifecycle state 38 and connections between KMPIs 16 with a "published" lifecycle state 44 and with a "work-in-progress lifecycle state 38 are invalid. FIG. 9c shows a resolution for the situation of FIG. 9b. The KMPI 16 of the third KMPE 54", previously connected with the now "retired" second KMPI 16' of the first KMPE 54 by a revision-specific KMPP 64, must also be retired. The KMPI 16 of the second KMPE 54', previously connected with the first KMPE 54 by a generic KMPP 62, must also be retired, since no valid target KMPI 16 exists within the KMPE. Whenever a KMPI 16 is moved into a terminal lifecycle state 46, 48, all KMPPs 60 originating from that KMPI 16 are replaced by revision-specific KMPPs 64. In this way a "snapshot" of the KMPPs 60 at the time of the termination of a KMPI 16 can advantageously be preserved. To enable maintenance of a connection between the first KMPE 54 (e.g. the newly created third KMPI 16" of the first KMPE 54) and the second KMPE 54', a new KMPI 16' must be created within the second KMPI 54' (see FIG. 9*d*). The newly created KMPI 16' of the second KMPI 54' is automatically attributed with the "work-in-progress" lifecycle state 38. A connection of a KMPI 16 with the "work-in-progress" lifecycle state 38 with a KMPE 54 comprising a KMPI 16 with at least a "work-in-progress" lifecycle state 38 is not prohibited by the KMPS 10.

The KMPPs 60 exist exclusively in the read-only component 70. The KMPPs 60 exist exclusively in the production content model. The declarative content model is free from KMPPs 60. The declarative content model instead comprises knowledge management platform associations (KMPAs, not shown). The KMPS 10 comprises at least one KMPA. The non-transitory memory unit 14 is configured to store KMPAs. Each KMPA is stored as a KMPI 16 within the repository 18 itself. The KMPAs are converted into KMPPs 60 upon a transformation of the respective KMPI 16 (or KMPE 54) from the authoring component 68 to the read-only component 70 (see also FIG. 2). The integrity checker module 52 is configured to automatically check an integrity of a newly created KMPP 60 upon a transition from the authoring component 68 to the read-only component 70, preventing the transition and/or prompting a warning in case an integrity violation is detected. The KMPAs are configured to define lightweight relations between KMPI 16 which are in non-terminal lifecycle states 38, 40, 42 different than the "published" lifecycle state 44. Preferably, the KMPAs are configured to define lightweight relations between KMPI 16 which are in the "work-in-progress" lifecycle state 38 and/or which are only accessible within the authoring component 68 and/or the collaboration component 80. Each of the KMPAs at least comprises information about a source KMPI 16, about a target KMPI 16' and about a concrete relation between the source KMPI 16 and the target KMPI 16'.

FIG. 10 shows a schematic process diagram of a computer-implemented knowledge management method with the KMPS 10. In at least one method step 66, permissions to access specific functions of the KMPS 10 are fine-grainedly set using the access control and permission management module 86. Thereby, users are at least divided into users who are authors and/or creators 78, into users who are collaborators 82 and into users who are end users 88. In a further method step 132, the KMPS 10 is organized according to the description above, in particular using the organized data structure comprising KMPIs 16, KMPTs 20, core KMPTs 22, 24, 26, 28, 30, KMPEs 54, KMPDs 58, designation types 112, 114, 116, KMPPs 60, 62, 64 and KMPAs as described above. In at least one partial method step 134 of the method step 132, KMPEs 54 comprising KMPIs 16 are created by authors and/or creators 78 using the authoring component 68. Alternatively or additionally, at least some KMPEs 54 or KMPIs 16 can be imported into the KMPS 10 using an import function of the KMPS 10. In a further partial method step 128 of the method step 132, the KMPIs 16 undergo a reviewing and approval process. The reviewing and approval process preferably comprises a discussion and/or a vote by subject matter experts and/or knowledge engineers. In a further partial method step 130 of the method step 132, at least some of the KMPIs 16 are approved for publishing and subsequently published in order to be accessible to the end user 88 with the read-only component 70. In a further method step 136, the end user 88 extracts knowledge data from the KMPS 10 and puts the knowledge to use.

REFERENCE NUMERALS

10 Knowledge management platform system
12 Processor
14 Memory unit
16 Knowledge management platform item
18 Repository
20 Knowledge management platform type
22 core KMPT
24 core KMPT
26 core KMPT
28 core KMPT
30 core KMPT
38 Lifecycle state
40 Lifecycle state
42 Lifecycle state
44 Lifecycle state
46 Lifecycle state
48 Lifecycle state
50 Lifecycle transition schema
52 Integrity checker module
54 Knowledge management platform entity
56 Inference unit
58 Knowledge management platform designation
60 Knowledge management platform pointers
62 Generic KMPP
64 Revision-specific KMPP
66 Method step
68 Authoring component
20 Read-only component
72 Cloud computing and/or cloud storage system
74 Access and/or authoring devices
76 Software-as-a-Service platform
78 Author and/or creator
80 Collaboration component
82 Collaborator
84 Contributor web services/administration environment
86 Access control and permission management module
88 End user
90 Consumer web services/administration environment
92 External source
94 Identity
96 Provenance
98 Name
100 Context
102 Revision number
104 Author- and/or creator-identity
106 Date
110 Source
112 Designation type
114 Designation type
116 Designation type
118 Validation rule
120 "Validation rule" KMPT
122 Audit log
124 Customized KMPT
126 Order
128 Partial method step
130 Partial method step
132 Method step
134 Partial method step
136 Method step

The invention claimed is:

1. A computer-implemented knowledge management platform system (KMPS), comprising
at least one processor and
a non-transitory memory unit that is at least configured
to store knowledge management platform items (KMPI) and
to include instructions which, when performed by the processor, cause an organization of the KMPI within a repository,
wherein several consecutive instances, in particular revisions, of the KMPI are grouped within the repository, thereby forming a knowledge management platform entity (KMPE),
wherein the KMPIs are allocated to knowledge management platform types (KMPT), which are components of a meta-modeled structure that
is stored within the non-transitory memory unit and
forms an ontology, with at least one of the KMPTs being implemented as a core KMPT,
wherein each core KMPT is attributed to each KMPI within the repository,
wherein each core KMPT defines an essential group of properties,
wherein the essential group of properties of the at least one core KMPT defines lifecycle states,
wherein the non-transitory memory unit is configured to store knowledge management platform pointers (KMPP),
each of which is assignable to at least one KMPI of a KMPE and
which are at least configured to link the at least one KMPI with at least one target KMPE within the repository and/or with at least one other KMPI within the repository,
wherein the meta-modeled structure is self-referential, such that each lifecycle state and each KMPP in turn is stored as a KMPI within the repository itself,
wherein at least one group of KMPPs is implemented as generic KMPPs,
wherein the non-transitory memory unit contains instructions which, when performed by the processor, induce an automatic updating of each generic KMPP pointing to a target KMPE upon detection of at least one revision of the target KMPE, the detection of the at least one revision of the target KMPE being implemented
as a detection of a change of a lifecycle state of the current revision with the highest precedence of the KMPIs of the KMPE and/or
as a detection of a change of a lifecycle state of a newer revision or instance of KMPIs of the KMPE into the lifecycle state with the same level of precedence or into the same lifecycle state,
wherein at least one further group of KMPPs is implemented as revision-specific KMPPs, which are configured to always point to a specific KMPI of a target KMPE, in particular even after a revision of the target KMPE,
wherein each KMPT is customizable,
wherein at least a customization of a KMPT itself is stored as a KMPI, and
wherein a customized KMPT inherits all customized and non-customized properties of the bequeathing KMPT.

2. The KMPS according to claim 1,
wherein the lifecycle states comprise at least one terminal lifecycle state and at least one non-terminal lifecycle state.

3. The KMPS according to claim 2,
wherein the lifecycle state of a KMPI with a terminal lifecycle state is immutable and/or
wherein the lifecycle state of a KMPI with a non-terminal lifecycle state is mutable, in particular into a "higher order" (higher precedence) lifecycle state or into a terminal lifecycle state.

4. The KMPS according to claim 1,
wherein the KMPIs which are defined as lifecycle states include at least one instruction which is to be considered when a KMPI attributed with a respective lifecycle state and stored within the repository is organized by the processor following instructions stored within the non-transitory memory unit.

5. The KMPS according to claim 2,
wherein KMPIs with a non-terminal lifecycle state within the repository are revisable,
wherein upon a revision of a KMPI with a non-terminal lifecycle state, a new instance and/or revision of the KMPI with a newly attributed lifecycle state is created and stored within the repository.

6. The KMPS according to claim 5, wherein several consecutive instances, in particular revisions, of the KMPIs are grouped within the repository, thereby forming a knowledge management platform entity (KMPE).

7. The KMPS according to claim 5, wherein the non-transitory memory unit contains instructions which, when performed by the processor during organizing of the repository, prevent a modification of the KMPIs, except for attributed metadata, unless a specific non-terminal lifecycle state, defined as a "work-in-progress" lifecycle state, is attributed to the KMPIs.

8. The KMPS according to claim 5,
wherein the new instance of the KMPI, in particular the new revision of the KMPI, created and stored upon the revision of the KMPI, is attributed a non-terminal "initial" lifecycle state.

9. The KMPS according to claim 6,
wherein an ensemble of all lifecycle states forms a lifecycle transition schema, which in particular defines accessibility pathways for the KMPS when accessing a KMPE.

10. The KMPS according to claim 9,
wherein the lifecycle transition schema is customizable and/or
wherein a plurality of lifecycle transition schemas exists simultaneously, in particular for KMPIs attributed with different KMPTs.

11. The KMPS according to claim 6,
wherein at least one lifecycle state is only attributable to one single KMPI of a KMPE within the repository at one time.

12. The KMPS according to claim 6,
wherein a lifecycle state of a first KMPI having a non-terminal lifecycle state and belonging to a KMPE is automatically changed into a terminal lifecycle state according to the lifecycle transition schema when a second KMPI belonging to the same KMPE is attributed a "new" lifecycle state that is identical to the lifecycle state of said first KMPI.

13. The KMPS according to claim 1,
wherein the lifecycle state of a KMPI within the repository defines if a connection and/or a linking of the KMPI to another KMPI within the repository is permitted or not.

14. The KMPS according to claim 1, comprising
an integrity checker module, which is configured to check the integrity of a newly created and/or newly revised KMPI and/or of an existing KMPI which was attributed with a new lifecycle state,
wherein upon detection of a violation of the integrity, a storing of the newly created KMPI within the repository and/or a change of the lifecycle state of the existing KMPI is prevented.

15. The KMPS according to claim 14,
wherein an execution of at least one checking procedure of the integrity checker module for a specific KMPI depends on the lifecycle state of said KMPI.

16. The KMPS according to claim 14,
wherein the non-transitory memory unit contains at least one validation rule which is executed by the processor during an integrity check by the integrity checker module,
wherein validation rules are customizable, wherein at least a customization of a validation rule itself is stored as a KMPI, and
wherein a specific KMPT is allocated to each of said KMPIs containing at least one validation rule.

17. The KMPS according to claim 14,
wherein the integrity checker module comprises an inference unit, in particular at least a (extensible and/or customizable) semantic inference unit, which is configured to evaluate logical expressions within a KMPI, within a set of KMPI and/or within the whole repository, and/or which is configured to evaluate or reason over a KMPI with related KMPIs and/or with attributes of the related KMPIs.

18. The KMPS according to claim 1,
wherein modifications to KMPIs, revisions of KMPIs, inactivation processes of KMPIs and or creation processes of KMPIs are tracked and secured via a blockchain.

19. The KMPS according to claim 1,
wherein at least one knowledge management platform designation (KMPD), which is stored within the repository and has at least one designation type, in particular a name, a code and/or a symbol, is attributed to at least one KMPI, in particular to at least one KMPE.

20. The KMPS according to claim 19,
wherein a number of KMPDs which are attributable to the at least one KMPI, in particular the at least one KMPE, is unlimited.

21. The KMPS according to claim 1,
wherein the lifecycle state of the at least one KMPI within the repository defines whether an assignment of a specific KMPP to the at least one KMPI and/or a pointing of the specific KMPP to a target KMPI and/or KMPE is permitted or not.

22. The KMPS according to claim 21,
wherein a KMPP assigned to a KMPI of a KMPE is only permitted to point to other KMPEs with compatible lifecycle states.

23. The KMPS according to claim 1, comprising
at least one knowledge management platform association (KMPA), which in particular is configured to define an ad-hoc or non-definitional relation, and which is stored as a KMPI within the repository itself,
wherein the KMPA at least comprises information about a source KMPI, about a target KMPI and about a relation between the source KMPI and the target KMPI.

24. The KMPS according to claim 23, comprising
an authoring component and a read-only component, wherein the KMPA is converted into a KMPP upon a transformation from the authoring component to the read-only component.

25. The KMPS according to claim 24, comprising
an integrity checker module, which is configured to automatically check the integrity of KMPPs created by inference upon a transition from the authoring component to the read-only component, preventing the transition and/or prompting a warning in case an integrity violation is detected.

26. A computer-implemented knowledge management method with a knowledge management platform system (KMPS), comprising
at least one processor and
a non-transitory memory unit that
stores knowledge management platform items (KMPI) and
includes instructions which, when performed by the processor, induce the KMPS to organize the KMPIs within a repository,
wherein several consecutive instances, in particular revisions, of the KMPI are grouped within the repository, thereby forming a knowledge management platform entity (KMPE),
wherein the KMPIs are allocated to knowledge management platform types (KMPT), which are components of a meta-modeled structure that
is stored within the non-transitory memory unit and forms an ontology,
wherein at least one of the KMPTs is implemented as a core KMPT,
wherein each core KMPT is attributed to each KMPI within the repository,
wherein each core KMPT defines an essential group of properties,
wherein the group of properties of the at least one core KMPT defines lifecycle states,
wherein the non-transitory memory unit stores knowledge management platform pointers (KMPP),
which are assigned to KMPIs of KMPEs and
which link the KMPIs with target KMPEs within the repository and/or with other KMPIs within the repository,
wherein the meta-modeled structure is self-referential and, as a result of this, each lifecycle state and each KMPP is in turn stored as a KMPI within the repository itself,
wherein at least one group of KMPPs is implemented as generic KMPPs,
wherein the non-transitory memory unit contains instructions which, when performed by the processor, induce an automatic updating of each generic KMPP pointing to a target KMPE upon detection of at least one revision of the target KMPE, the detection of the at least one revision of the target KMPE being implemented
as a detection of a change of a lifecycle state of the current revision with the highest precedence of the KMPIs of the KMPE and/or
as a detection of a change of a lifecycle state of a newer revision or instance of KMPIs of the KMPE into the lifecycle state with the same level of precedence or into the same lifecycle state,
wherein at least one further group of KMPPs is implemented as revision-specific KMPPs, which are configured to always point to a specific KMPI of a target KMPE, in particular even after a revision of the target KMPE, wherein each KMPT is customizable, wherein at least a customization of a KMPT itself is stored as a KMPI, and wherein a customized KMPT inherits all customized and non-customized properties of the bequeathing KMPT.

\* \* \* \* \*